(12) United States Patent
Moriya et al.

(10) Patent No.: US 7,485,647 B2
(45) Date of Patent: Feb. 3, 2009

(54) 2-AMINOQUINOLINE DERIVATIVES

(75) Inventors: Minoru Moriya, Tsukuba (JP); Takao Suzuki, Tsukuba (JP); Akane Ishihara, Tsukuba (JP); Hisashi Iwaasa, Tsukuba (JP); Akio Kanatani, Ushiku (JP)

(73) Assignee: Banyu Pharmaceutical Co., Ltd., Tokyo (JP)

( * ) Notice: Subject to any disclaimer, the term of this patent is extended or adjusted under 35 U.S.C. 154(b) by 529 days.

(21) Appl. No.: 10/556,932

(22) PCT Filed: May 20, 2004

(86) PCT No.: PCT/JP2004/007217

§ 371 (c)(1), (2), (4) Date: Nov. 16, 2005

(87) PCT Pub. No.: WO2004/103992

PCT Pub. Date: Dec. 2, 2004

(65) Prior Publication Data

US 2006/0287340 A1    Dec. 21, 2006

(30) Foreign Application Priority Data

May 21, 2003  (JP) .............................. 2003-143398

(51) Int. Cl.
C07D 401/12 (2006.01)
C07D 401/14 (2006.01)
A61K 31/506 (2006.01)

(52) U.S. Cl. ...................................... 514/256; 544/333

(58) Field of Classification Search ................ 544/333; 514/256

See application file for complete search history.

(56) References Cited

FOREIGN PATENT DOCUMENTS

| EP | 1 285 651 | 2/2003 |
|----|-----------|--------|
| WO | WO 95/32967 | 12/1995 |
| WO | WO 99/48492 | 9/1999 |
| WO | WO 00/64877 | 11/2000 |
| WO | WO 01/21577 | 3/2001 |
| WO | WO 02/02744 | 1/2002 |
| WO | WO 03/045313 | 6/2003 |

OTHER PUBLICATIONS

Simone, Oncology: Introduction, Cecil Textbook of Medicine, 20th Edition, vol. 1, pp. 1004-1010, 1996.*

Kowalski et al., Exp. Opin. Investig. Drugs, vol. 13 (2004), pp. 1113-1122, "Therapeutic potential of melanin-concentrating hormone-1 receptor antagonists for the treatment of obesity".

Clark et al., J. Med. Chem., vol. 47 (2004), pp. 3962-3971, "A virtual screening approach to finding novel and potent antagonists at the melanin-concentrating hormone 1 receptor".

Arienzo et al., Bioorg. & Medicinal Chem. Letters, vol. 14 (2004), pp. 4099-4102, Structure-activity relationshps of a novel series of melanin-concentrating hormone (MCH) receptor antagonists.

Kato et al., Chem. Abstracts, 134:266103, "Preparation of N-tetrahydronapththalenyl carboxamides as melanin concentrating hormone antagonists", 2001.

Antelman et al., Chem. Abstracts, 91:68543, "The importance of stress in assessing the effects of anorectic drugs", 1979.

Mueller et al., Chem. Abstracts 138:4532, "Preparation of quinolines as ligands for the neuropeptide Y receptor useful against arthritis, cardiovascular diseases, diabetes, renal failure, eating disordes and obesity" 2002.

* cited by examiner

Primary Examiner—Deepak Rao
(74) Attorney, Agent, or Firm—Janet E. Fair; Catherine D. Fitch

(57) ABSTRACT

This invention provides 2-aminoquinoline derivatives represented by a general formula [I]

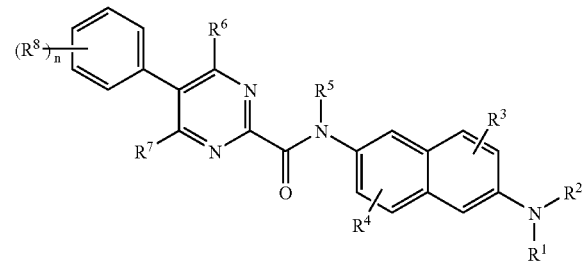

[I]

[in which $R^1$ and $R^2$ either stand for lower alkyl, lower cycloalkyl, etc., or $R^1$ and $R^2$ together form an aliphatic nitrogen-containing heterocycle with the nitrogen atom to which they bind; $R^3$, $R^4$, $R^5$, $R^6$ and $R^7$ stand for hydrogen, lower alkyl, etc.; $R^8$ stands for lower alkyl, lower alkyloxy, etc.; and n stands for an integer of 0-4]. The compounds act as melanin concentrating hormone receptor antagonist, and are useful as medicines for central nervous system disorders, cardiovascular disorders and metabolic disorders.

11 Claims, 1 Drawing Sheet

2-AMINOQUINOLINE DERIVATIVES

CROSS-REFERENCE TO RELATED APPLICATIONS

This application is a U.S. National Phase application under 35 U.S.C. §371 of PCT Application No. PCT/JP2004/007217, filed May 20, 2004, which claims priority under 35 U.S.C. §365(b) from Japanese patent application No. JP2003-143398, filed May 21, 2003.

TECHNICAL FIELD

This invention relates to 2-aminoquinoline derivatives which are useful in the field of medicines. Said compounds act as antagonists to melanin concentrating hormone receptor, and are useful as preventing or treating agents of various diseases of cardiovascular system, nervous system, metabolic systems, reproductive system, respiratory system, digestive system and the like.

BACKGROUND ART

Melanin concentrating hormone (hereafter abbreviated as "MCH") is a cyclic peptide hormone/neuro-peptide, which was for the first time isolated by Kawauchi, et al. in 1983 from sermon hypophysis [Nature, Vol. 305, 321 (1983)]. The hormone is known to functionally antagonize to melanin cell stimulating hormone in fishes, to cause concentration of melanin granules in melanophore and participate in body color change [International Review of Cytology, Vol. 126, 1(1991); Trends in Endocrinology and Metabolism, Vol. 5, 120 (1994)]. Also in mammals, MCH-containing neuron nerve cells are localized in the hypothalamus lateral field and uncertain zone, but their nerve fibers are projecting over a very wide scope in the brain [The Journal of Comparative Neurology, Vol. 319, 218 (1992)], and MCH is considered to preside over various central functions in living bodies.

Hypothalamus lateral field is known of old as feeding center, and furthermore, recently molecular biological and pharmacological knowledge suggesting participation of MCH in controlling energetic homeostasis are being accumulated. That is, it has been reported that expression of mRNA, which is a MCH precursor, was accelerated in brains of ob/ob mouse, db/db mouse, $A^y$/a mouse, Zucker fatty rat or the like which are model animals of hereditary obesity, or in brains of fasted mice [Nature, Vol. 380, 243 (1996); Diabetes, Vol. 47, 294 (1998); Biochemical and Biophysical Research Communications, Vol. 268, 88 (2000); Molecular Brain Research, Vol. 92, 43 (2000)].

Acute ventricular administration of MCH to rats was observed to induce accelerated feeding activity [Nature, Vol. 380, 243 (1996)] and chronic administration invites obesity accompanied by polyphagy [Proceedings of the National Academy of Science of the United States of America, Vol. 99, 3240, (2002)]. Moreover, MCH precursor gene-deficient mouse shows reduced food ingestion or rise in oxygen consumption per body weight compared to wild type mice. Its low body weight due to decrease in body fat was observed [Nature, Vol. 396, 670 (1998)].

On the contrary, the transgenic mouse which expresses excessive MCH precursor develops obesity accompanied by polyphagy and insulin resistance [The Journal of Clinical Investigation, Vol. 107, 379 (2001)]. Consequently, it is suggested that MCH is an important factor for developing obesity and participates in diseases induced by metabolic disorder or respiratory diseases of which one of risk factors is obesity.

Besides, MCH is known to participate also in anxiety-causing action, epilepsy, memory, learning, diuretic action, excretory action of sodium and potassium, oxytocin secreting action, reproduction and reproductive function [Peptides, Vol. 17, 171 (1996); Peptides, Vol. 18, 1095 (1997), Peptides, Vol, 15, 757 (1994); Journal of Neuroendocrinology, Vol. 8, 57 (1996); Critical Reviews in Neurobiology, Vol. 8, 221, (1994)].

MCH causes versatile pharmacological actions through MCH receptors which are present mainly in the central nervous system. As receptors of MCH, at least two types of type 1 receptors (MCH-1R or SLC-1) and type 2 receptors (MCH-2R or SLT) are known [Nature, Vol. 400, 261 (1999); Nature, Vol. 400, 265 (1999); Biochemical and Biophysical Research Communications, Vol. 261, 622 (1999); Nature Cell Biology, Vol. 1, 267 (1999); FEBS Letters, Vol. 457, 522 (1999); Biochemical and Physical Research Communications, Vol. 283, 1013 (2001); The Journal of Biological Chemistry, Vol. 276, 20125 (2001); Proceedings of the National Academy of Sciences of the United States of America, Vol. 98, 7564 (2001); Proceedings of the National Academy of Sciences of the United States of America, Vol. 98, 7576 (2001); The Journal of Biological Chemistry, Vol. 276, 34664 (2001); and Molecular Pharmacology, Vol. 60, 632 (2001)].

Of those, the pharmacological action observed on rodents is induced mainly via MCH-1R [Genomics, Vol. 79, 785 (2002)]. Because MCH-1R gene-deficient mice chronically administered with MCH do not develop polyphagy or obesity, it is known that controlling of energy exchange by MCH is induced via MCH-1R. Furthermore, deficiency of MCH-LR promotes activity amount of mouse [Proceedings of the National Academy of Sciences of the United States of America, Vol. 99, 3240 (2002)], and its participation in central diseases accompanied by behavioral disorder, for example, attention-deficit hyperactivity disorder, schizophrenia and the like also is strongly suggested [Molecular Medicine Today, Vol. 6, 43 (2000); Trends in Neuroscience, Vol. 24, 527 (2001)].

It is also reported that autoantibody to MCH-1R is present in serum of vitiligo vulgaris patient [The Journal of Clinical Investigation, Vol. 109, 923 (2002)]. Furthermore, expression of MCH-1R in certain species of cancer cells was reported, and in vivo expression sites of MCH and MCH-1R also suggest their participation in cancer, sleep, vigil, drug dependence and digestive disorders [Biochemical and Biophysical Research Communications, Vol. 289, 44 (2001); Neuroendocrinology, Vol. 61, 348 (1995); Endocrinology, Vol. 137, 561 (1996); The Journal of Comparative Neurology, Vol. 435, 26 (2001)].

Functions of MCH are expressed upon its binding to MCH receptors. Therefore, when its binding to MCH receptor is inhibited, expression of MCH action can be inhibited. In consequence, substances which are antagonists to binding of MCH to its receptor are useful as preventing or treating agent of those various diseases in which MCH participates, for example, metabolic disorders represented by obesity, diabetes, hormone disorder, hyperlipidemia, gout, fatty liver, hepatitis and cirrhosis; cardiovascular disorders, represented by stenocardia, acute or congestive heart failure, myocardial infarction, coronary atherosclerosis, hypertension, renal diseases and electrolyte abnormality; central nervous system or peripheral nervous system disorders represented by bulimia, emotional disturbance, depression, anxiety, epilepsy, delirium, dementia, schizophrenia, attention-deficit hyperactivity disorder, memory impairment, sleep disorders, cognitive failure, dyskinesia, paresthesias, smell disorders, morphine tolerance, drug dependence and alcoholism;

reproductive disorders represented by infertility, preterm labor and sexual dysfunction; digestive disorders; respiratory disorders; cancer or pigmentation.

Concerning heretofore known melanin concentration hormone receptor antagonists, for example, International Publications WO 01/21577, WO 02/06245, WO 02/02744 and WO 01/82925; and JP 2002-3370A contain relevant disclosures.

For instance, JP2002-3370A disclosed the following compounds:

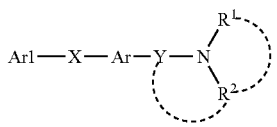

However, according to its specification, the Ar moiety is a monocyclic aromatic ring and does not include quinoline ring which is a bicyclic aromatic ring conceived for the present invention. Furthermore, as the moiety corresponding to Ar1, phenylpyrimidine ring which is characteristic to the derivatives of the present invention is not disclosed. Thus the compounds differ from the derivatives of the present invention in structure. Still in addition, it is by no means easy to conceive based on the specification adoption of bicyclic aromatic quinoline ring as the Ar and phenylpyrimidine skeletal structure as the Ar1 moiety, in combination.

Also WO 01/82925 disclosed the following compounds:

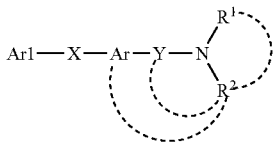

However, in the compounds represented by the above formula, $Y(C_1-C_6$ spacer) is present between Ar and amino group, and they differ from the compounds of the present invention in structure.

The object of the present invention is to provide 2-aminoquinoline derivatives which have an action to inhibit binding of MCH to MCH-1R, and also to provide preventing or treating agents utilizing them, of diseases such as metabolic disorders represented by obesity, diabetes, hormone disorder, hyperlipidemia, gout, fatty liver, hepatitis and cirrhosis; cardiovascular disorders, represented by stenocardia, acute or congestive heart failure, myocardial infarction, coronary atherosclerosis, hypertension, renal diseases and electrolyte abnormality; central nervous system or peripheral nervous system disorders represented by bulimia, emotional disturbance, depression, anxiety, epilepsy, delirium, dementia, schizophrenia, attention-deficit hyperactivity disorder, memory impairment, sleep disorders, cognitive failure, dyskinesia, paresthesias, smell disorders, morphine tolerance, drug dependence and alcoholism; reproductive disorders represented by infertility, preterm labor and sexual dysfunction; digestive disorders; respiratory disorders; cancer or pigmentation.

DISCLOSURE OF THE INVENTION

We have engaged in concentrative studies with the view to develop compounds which inhibit binding of MCH to MCH-1R, to discover that those compounds of quinoline skeletal structure having an amino group at the 2-position, with a specific phenylpyrimidine group bound to the 6-position via an amide group were novel substances, have MCH-1R antagonistic action and excel in pharmacolinetics. Based on this knowledge, the present invention is completed.

Accordingly, therefore, the present invention provides:
(1) 2-aminoquinoline derivatives represented by a general formula [I]

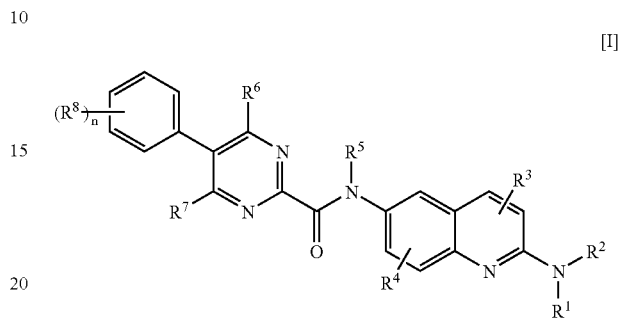

[in which $R^1$ and $R^2$ each independently stands for a substituent selected from the group consisting of
1) optionally hydroxyl- or halogen-substituted lower alkyl,
2) optionally $R^9$-substituted 3 to 6-membered cycloalkyl, and
3) optionally $R^9$-substituted 4 to 6-membered heterocycloalkyl, or
4) $R^1$ and $R^2$ together form a 4 to 11-membered crosslinking, non-crosslinking or spiro ring aliphatic nitrogen-containing heterocycle, with the nitrogen atom to which they bind, one or two optional hydrogen atoms in the aliphatic nitrogen-containing heterocycle being optionally substituted with $R^9$;
$R^3$, $R^4$, $R^6$ and $R^7$ each independently stands for a substituent selected from the group consisting of
1) hydrogen,
2) hydroxyl,
3) halogen, and
4) optionally halogen-substituted lower alkyl;
$R^5$ stands for
1) hydrogen, or
2) optionally halogen-substituted lower alkyl;
$R^8$ stands for a substituent selected from the group consisting of
1) halogen,
2) lower alkyl, and
3) lower alkyloxy;
$R^9$ stands for a substituent selected from the group consisting of hydroxyl, amino, mono-lower alkylamino, di-lower alkylamino, optionally hydroxyl- or halogen-substituted lower alkyl, (lower alkyloxycarbonyl)amino, lower alkyloxycarbonyl-(lower alkyl)amino, lower alkylcarbonylamino, lower alkylcarbonyl(lower alkyl)amino, mono-lower alkylcarbamoyl (lower alkyl) amino, di-lower alkylcarbamoyl(lower alkyl)amino, lower alkylsulfonylamino, lower alkylsulfonyl(lower alkyl)amino, oxo and 2-oxopyrrolidinyl; and
n is 0, 1, 2, 3 or 4]

or their pharmaceutically acceptable salts.

The invention furthermore provides:
(2) melanin concentrating hormone receptor antagonists containing the compounds described in (1) above as the active ingredient;

(3) preventing or treating agents containing the compounds described in (1) above as the active ingredient, of diseases such as metabolic disorders represented by obesity, diabetes, hormone disorder, hyperlipidemia, gout, fatty liver, hepatitis and cirrhosis; cardiovascular disorders, represented by stenocardia, acute or congestive heart failure, myocardial infarction, coronary atherosclerosis, hypertension, renal diseases and electrolyte abnormality; central nervous system or peripheral nervous system disorders represented by bulimia, emotional disturbance, depression, anxiety, epilepsy, delirium, dementia, schizophrenia, attention-deficit hyperactivity disorder, memory impairment, sleep disorders, cognitive failure, dyskinesia, paresthesias, smell disorders, morphine tolerance, drug dependence and alcoholism; reproductive disorders represented by infertility, preterm labor and sexual dysfunction; digestive disorders; respiratory disorders; cancer or pigmentation.

(4) medical composition containing the compounds described in (1) above or their pharmaceutically acceptable salts and medically acceptable carriers;

(5) a process for preparing the compounds represented by the general formula [I]

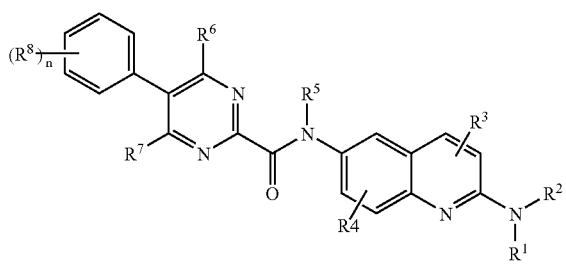

[in which $R^1$, $R^2$, $R^3$, $R^4$, $R^5$, $R^6$, $R^7$, $R^8$ and n have the same significations as given in (1) above], which comprises a step of subjecting a compound of a general formula [II]

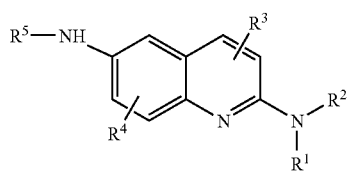

[in which $R^1$, $R^2$, $R^3$, $R^4$ and $R^5$ have the same significations as given in (1) above] and a compound of a general formula [III]

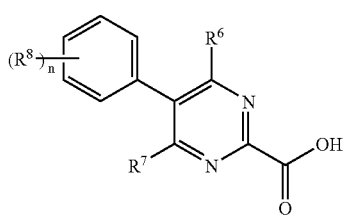

[in which $R^6$, $R^7$, $R^8$ and n have the same significations as given in (1) above] to an amidation reaction.

Hereinafter the codes and terms used in the present specification are explained.

As "halogen", fluorine, chlorine, bromine and iodine can be named.

"Lower alkyl" includes $C_1$-$C_6$ alkyl, i.e., $C_1$-$C_6$ straight chain alkyl and $C_3$-$C_6$ branched chain alkyl, specific examples being methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl, 1-ethyl-1-methylpropyl and the like.

"Lower cycloalkyl" includes $C_3$-$C_6$ cycloalkyl, specific examples being cyclopropyl, cyclobutyl, cyclopentyl and cyclohexyl.

"Lower cycloalkyloxy" signifies those groups in which $C_3$-$C_6$ cycloalkyl binds to oxygen, specific examples being cyclopropyloxy, cyclobutyloxy, cyclopentyloxy and cyclohexyloxy.

"Lower heterocycloalkyl" signifies $C_3$-$C_6$ cycloalkyl group in which optional one or two carbon atoms are substituted with nitrogen, oxygen or sulfur, specific examples including azetidinyl, pyrrolidinyl, piperidinyl, piperazinyl, tetrahydrofuranyl, tetrahydropyranyl, morpholinyl, 1-thia-4-azacyclohexyl and the like.

"Oxo" signifies a group in which two substituent groups form carbonyl group with the carbon atom to which they bind. For example, as to $R^5$, it refers to the case where two $R^5$s and the carbon atom to which they bind form a carbonyl group.

"Optionally fluorine-substituted lower alkyl" includes lower alkyl and fluorine-substituted lower alkyl, specific examples being, besides above-named lower alkyl groups, fluoromethyl, difluoromethyl, trifluoromethyl, 1,2-difluoroethyl, and the like.

"Optionally halogen-substituted lower alkyl" includes lower alkyl and halogen-substituted lower alkyl, specific examples being, besides above-named lower alkyl groups, fluoromethyl, difluoromethyl, trifluoromethyl, 1,2-difluoroethyl, chloromethyl, dichloromethyl, trichloromethyl, 1,2-dichloroethyl, and the like.

"Optionally fluorine-substituted lower alkyloxy" includes those group in which lower alkyl or fluorine-substituted lower alkyl binds to oxygen, specific examples being: as lower alkoxy, methoxy, ethoxy, n-propyloxy, isopropyloxy, n-butyloxy, isobutoxy, tert-butoxy, n-pentyloxy and the like; and as fluorine-substituted lower alkyloxy, fluoromethoxy, difluoromethoxy, trifluoromethoxy, 1,2-difluoroethoxy, and the like.

"Mono-lower alkylamino" is an amino in which one of its hydrogen atoms is substituted with a lower alkyl, specific examples being methylamino, ethylamino, n-propylamino, isopropyl amino, n-butylamino, sec-butylamino, tert-butylamino, and the like.

"Di-lower alkylamino" signifies an amino whose two hydrogen atoms are substituted with lower alkyl groups, specific examples being dimethylamino, diethylamino, ethylmethylamino, di(n-propyl)amino, methylpropylamino, diisopropylamino, and the like.

"Lower alkyloxycarbonyl" signifies lower alkyloxy-substituted carbonyl, e.g., $C_1$-$C_6$ alkyloxycarbonyl, specific examples being methoxycarbonyl, ethoxycarbonyl, n-propyloxycarbonyl, isopropyloxycarbonyl, n-butyloxycarbonyl, isobutoxycarbonyl, tert-butoxycarbonyl, n-pentyloxycarbonyl, and the like.

"Lower alkyloxycarbonylamino" is an amino to which lower alkyloxycarbonyl is bound, which includes $C_1$-$C_6$ alkyloxycarbonyl-amino, specific examples being methoxycarbonylamino, ethoxycarbonylamino, n-propyloxycarbonylamino, isopropyloxy-carbonylamino, n-butoxycarbonylamino, isobutoxycarbonylamino, tert-butoxycarbonylamino, n-pentyloxycarbonylamino, and the like.

"Lower alkyloxycarbonyl (lower alkyl)amino" is a mono-lower alkylamino whose hydrogen on the nitrogen atom is substituted with a lower alkyloxycarbonyl, specific examples being methoxycarbonyl(methyl)amino, ethoxycarbonyl(methyl)amino, n-propyloxycarbonyl(methyl)amino, and the like.

"Lower alkylcarbonyl" is a carbonyl to which lower alkyl is bound, e.g. $C_1$-$C_6$ alkylcarbonyl, specific examples being acetyl, propionyl, butyryl, isobutyryl, valeryl, isovaleryl, pivaloyl, and the like.

"Lower alkylcarbonylamino" is an amino to which lower alkylcarbonyl is bound, specific examples being acetamino, propionylamino, isobutyrylamino, valerylamino, isovalerylamino, pivaloylamino and the like.

"Lower alkylcarbonyl(lower alkyl)amino" is a lower alkylamino in which the hydrogen on its nitrogen atom is substituted with lower alkylcarbonyl, specific examples including methylcarbonyl(methyl)amino, ethylcarbonyl(methyl)amino, n-propylcarbonyl(methyl)amino, and the like.

"Lower alkylcarbonyloxy" is a group in which a lower alkylcarbonyl is bound to oxygen, specific examples including acetoxy, propionyloxy, valeryloxy, isovaleryloxy, pivaloyloxy, and the like.

"Mono-lower alkylcarbamoyl" is a carbamoyl one of whose hydrogen atoms is substituted with lower alkyl, specific examples including methylcarbamoyl, ethylcarbamoyl, n-propylcarbamoyl, isopropylcarbamoyl, n-butylcarbamoyl, sec-butylcarbamoyl, tert-butylcarbamoyl, and the like.

"Di-lower alkylcarbamoyl" is a carbamoyl whose two hydrogen atoms are substituted with lower alkyl groups, specific examples including dimethylcarbamoyl, diethylcarbamoyl, ethylmethylcarbamoyl, di(n-propyl)carbamoyl, methylpropylcarbamoyl, diisopropylcarbamoyl, and the like.

"Mono-lower alkylcarbamoylamino" is an amino one of whose hydrogen atoms is substituted with mono-lower alkylcarbamoyl group, specific examples including methylcarbamoylamino, ethylcarbamoyl-amino, n-propylcarbamoylamino, isopropylcarbamoylamino, n-butylcarbamoylamino, sec-butylcarbamoylamino, tert-butylcarbamoylamino, and the like.

"Di-lower alkylcarbamoylamino" is an amino one of whose hydrogen atoms is substituted with di-lower alkylcarbamoyl, specific examples including dimethylcarbamoylamino, diethylcarbamoylamino, di(n-propyl)carbamoylamino, diisopropylcarbamoylamino, di(n-butyl)carbamoylamino, di(sec-butyl)carbamoylamino, di(tert-butyl)carbamoylamino, and the like.

"Mono-lower alkylcarbamoyl(lower alkyl)amino" is a lower alkylamino whose hydrogen on the nitrogen atom is substituted with mono-lower alkylcarbamoyl, specific examples including monomethylcarbamoyl(methyl)amino, monoethylcarbamoyl(methyl)-amino, mono(n-propyl)carbamoyl(methyl)amino, and the like.

"Di-lower alkylcarbamoyl(lower alkyl)amino" is a lower alkylamino whose one hydrogen atom on the nitrogen atom is substituted with di-lower alkylcarbamoyl, specific examples including dimethylcarbamoyl(methyl)amino, diethylcarbamoyl(methyl)amino, di(n-propyl)carbamoyl(methyl)amino, and the like.

"Mono-lower alkylcarbamoyloxy" is a group in which a mono-lower alkylcarbamoyl is bound to oxygen, specific examples including methylcarbamoyloxy, ethylcarbamoyloxy, n-propylcarbamoyloxy, isopropylcarbamoyloxy, n-butylcarbamoyloxy, sec-butylcarbamoyloxy, tert-butylcarbamoyloxy, and the like.

"Di-lower alkylcarbamoyloxy" is a group in which di-lower alkylcarbamoyl is bound to oxygen, specific examples including dimethylcarbamoyloxy, diethylcarbamoyloxy, ethylmethyl-carbamoyloxy, di(n-propyl)carbamoyloxy, methylpropylcarbamoyloxy, diisopropylcarbamoyloxy, and the like.

"Lower alkylsulfonyl" is a group in which lower alkyl is bound to sulfonyl, specific examples including methylsulfonyl, ethylsulfonyl, n-propylsulfonyl, isopropylsulfonyl, n-butylsulfonyl, sec-butylsulfonyl, tert-butylsulfonyl, and the like.

"Lower alkylsulfonylamino" is an amino one of whose hydrogen atoms is substituted with lower alkylsulfonyl, specific examples including methylsulfonylamino, ethylsulfonylamino, n-propylsulfonylamino, isopropylsulfonylamino, n-butylsulfonylamino, sec-butylsulfonylamino, tert-butylsulfonylamino, and the like.

"Mono-lower alkylsulfamoyl" is a sulfamoyl one of whose hydrogen atoms is substituted with lower alkyl, specific examples including monomethylsulfamoyl, monoethylsulfamoyl, mono(n-propyl)sulfamoyl, monoisopropylsulfamoyl, mono(n-butyl)-sulfamoyl, mono(sec-butyl)sulfamoyl, mono(tert-butyl)sulfamoyl, and the like.

"Di-lower alkylsulfamoyl" is a sulfamoyl whose two hydrogen atoms are substituted with lower alkyl groups, specific examples including dimethylsulfamoyl, diethylsulfamoyl, di(n-propyl)sulfamoyl, diisopropylsulfamoyl, di(n-butyl)sulfamoyl, di(sec-butyl)sulfamoyl, di(tert-butyl)sulfamoyl, and the like.

"Mono-lower alkylsulfamoylamino" is an amino one of whose hydrogen atoms is substituted with a lower alkylsulfamoyl, specific examples including monomethylsulfamoylamino, monoethylsulfamoylamino, mono(n-propyl)sulfamoylamino, monoisopropylsulfamoyl-amino, mono(n-butyl)sulfamoylamino, mono(sec-butyl)-sulfamoylamino, tert-butylsulfamoylamino, and the like.

"Di-lower alkylsulfamoylamino" is an amino one of whose hydrogen atoms is substituted with di-lower alkylsulfamoyl, specific examples including dimethylsulfamoylamino, diethylsulfamoylamino, ethylmethylsulfamoylamino, di(n-propyl)sulfamoylamino, methylpropylsulfamoylamino, diisopropylsulfamoylamino, and the like.

"Mono-lower alkylsulfamoyl(lower alkyl)amino" is a "mono-lower alkylamino" whose hydrogen on the nitrogen atom is substituted with lower alkylsulfamoyl, specific examples including monomethylsulfamoyl(methyl)amino, monoethylsulfamoyl(methyl)-amino, mono(n-propyl)sulfamoyl(methyl)amino, and the like.

"Di-lower alkylsulfamoyl(lower alkyl)amino" is a "mono-lower alkylamino" whose hydrogen on the nitrogen atom is substituted with di-lower alkylsulfamoyl, specific examples including dimethylsulfamoyl(methyl)amino, diethylsulfamoyl(methyl)amino, di(n-propyl)sulfamoyl(methyl)amino, and the like.

As "4 to 11-membered crosslinking, non-crosslinking or spiro ring aliphatic nitrogen-containing heterocycle", for example, as crosslinking aliphatic nitrogen-containing heterocycle, 2,5-diazabicyclo[2.2.1]heptane, 2,5-diazabicyclo[2.2.2]octane, octahydropyrrolo[3.4-b] pyrrole, octahydropyrrolo[3.4-c]pyrrole, 3-azabicyclo[3.1.0]hexane, decahydropyrrolo[3,4-d]azepine, and the like can be named;

As non-crosslinking aliphatic nitrogen-containing heterocycle, azetidine ring, pyrrolidine ring, piperidine ring, hexamethylenimine ring, heptamethylenimine ring, morpholine ring, and the like can be named; and as spiro ring aliphatic nitrogen-containing heterocycle, 2-azaspiro[4.4]nonane, 1-oxa-7-azaspiro[4.4]nonane, 2-oxa-7-azaspiro[4.4]nonane, 1,7-diazaspiro[4.4]nonane, 3-oxa-1,7-diazaspiro[4.4]nonane, 2,7-diazaspiro[4.4]nonane, 2,7-diazaspiro[3.5]nonane, 2-azaspiro[3.3]heptane, 2-oxa-6-azaspiro[3.3]heptane, 2,8-diazaspiro[4.5]decane, and the like can be named.

"Pharmaceutically acceptable salts" of the compounds which are represented by the general formula [I] signify those customarily used salts which are permissible to be used in medicines, specific examples including acid addition salts at amino or acid addition salts at nitrogen-containing heterocycle.

As such acid addition salts, inorganic acid salts such as hydrochloride, sulfate, nitrate, phosphate, perchlorate and the like; organic acid salts such as maleate, fumarate, tartarate, citrate, ascorbate, trifluoroacetate and the like; and sulfonic acid salts such as methanesulfonate, isethionate, benzenesulfonate, p-toluenesulfonate, and the like can be named.

Compounds Represented by the General Formula [I]

In the compounds represented by the general formula [I], $R^1$ and $R^2$ each independently stands for a substituent selected from the group consisting of
1) optionally hydroxyl- or halogen-substituted lower alkyl,
2) optionally $R^9$-substituted 3 to 6-membered cycloalkyl, and
3) optionally $R^9$-substituted 4 to 6-membered heterocycloalkyl, or
4) $R^1$ and $R^2$ together form a 4 to 11-membered crosslinking, non-crosslinking or spiro ring aliphatic nitrogen-containig heterocycle, with the nitrogen atom to which they bind, one or two optional hydrogen atoms in the aliphatic nitrogen-containing heterocyclic being optionally substituted with $R^9$.

Specific examples of $R^1$ or $R^2$ include methyl, ethyl, n-propyl, isopropyl, hydroxymethyl, 2-hydroxyethyl, 3-hydroxypropyl, chloromethyl, fluoromethyl, difluoromethyl, trifluoromethyl, 2-fluoroethyl, 2-chloroethyl, cyclobutyl, cyclopentyl, cyclohexyl, tetrahydrofuran-2-yl, pyrrolidin-3-yl, N-acetylpyrrolidin-3-yl, N-methoxycarbonylpyrrolidin-3-yl, N-isopropylcarbonylpyrrolidin-3-yl, N-methylsulfonylpyrrolidn-3-yl, and the like.

When $R^1$ and $R^2$ together form 4 to 11-membered crosslinking, non-crosslinking or spiro ring nitrogen-containing aliphatic heterocycle, specific examples of the ring include azetidine, pyrrolidine, piperidine, morpholine, 2-azaspiro[4.4]nonane, 1-oxa-7-azaspiro[4.4]nonane, 2-oxa-7-azaspiro[4.4]nonane, 1,7-diazaspiro[4.4]nonane, 3-oxa-1,7-diazaspiro[4.4]nonane, 2,7-diazaspiro[4.4]nonane, 2,7-diazaspiro[3.5]nonane, decahydropyrrolo[3,4-d]azepine, 2-azaspiro[3.3]heptane, 2-oxa-6-azaspiro[3.3]heptane, 2,5-diazabicyclo[2.2.1]heptane, octahydropyrrolo[3,4-b]pyrrole, octahydropyrrolo[3.2-b]pyrrole, 3-azabicyclo[3.1.0]hexane, octahydropyrrolo[1.2-a]pyrazine, octahydropyrrolo[3,4-d]azepine, 2,8-diazaspiro[4.5]decane, and the like.

$R^9$ stands for a substituent selected from the group consisting of hydroxyl, amino, mono-lower alkylamino, di-lower alkylamino, optionally hydroxyl- or halogen-substituted lower alkyl, lower alkylcarbonylcarbonylamino, lower alkylcarbonylcarbonyl(lower alkyl)amino, lower alkylcarbonylamino, lower alkylcarbonyl(lower alkyl)amino, mono-lower alkylcarbamoyl(lower alkyl)amino, di-lower alkylcarbamoyl(lower alkyl)amino, lower alkylsulfonylamino, lower alkylsulfonyl(lower alkyl)amino, and 2-oxopyrrolidinyl.

Examples of preferred $R^9$ include methyl, ethyl, hydroxymethyl, hydroxyethyl, amino, t-butylcarbonylamino, t-butylcarbonyl(methyl)-amino, methylamino, ethylamino, isopropyl(methyl)amino, 1-methyl-1-aminoethyl, 1-methyl-1-hydroxyethyl, methylcarbonyl-(methyl)amino, methylcarbonyl(ethyl)amino, ethylcarbonyl(methyl)-amino, ethylcarbonyl(ethyl)amino, isopropylcarbonyl(methyl) amino, isopropylcarbonyl(ethyl)amino, methoxycarbonyl (methyl)amino, ethoxycarbonyl(methyl)amino, t-butyloxycarbonylamino, methylsulfonyl(methyl)amino, methylsulfonyl(ethyl)amino, ethylsulfonyl(methyl)amino, dimethylsulfamoyl(methyl)amino, dimethylcarbamoyl, dimethylcarbamoyl(methyl)amino, 2-oxopyrrolidinyl, 2-oxo-oxazolidin-3-yl, and the like.

Preferred $R^1$ or $R^2$ include methyl, ethyl, n-propyl, isopropyl, hydroxymethyl, 2-hydroxyethyl, 3-hydroxypropyl, tetrahydrofuran-2-yl, pyrrolidin-3-yl, N-acetylpyrrolidin-3-yl, N-methoxycarbonylpyrrolidin-3-yl, N-isopropylcarbonylpyrrolidin-3-yl, N-methylsulfonylpyrrolidin-3-yl, and the like.

As the aliphatic nitrogen-containing heterocycle formed by $R^1$ and $R^2$ together with the nitrogen atom to which they bind, preferably those substituent groups represented by a formula (A)

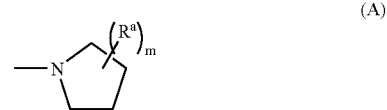

(A)

[in which $R^a$ either stands for $R^9$ or two $R^a$s together form —(CH$_2$)x-(NH)—(CH$_2$)-, optional hydrogen in the substituent group may optionally be substituted with lower alkyl, lower alkylcarbonyl or oxo, x and y each independently stands for 0, 1, 2, 3 or 4 while satisfying the range specified by $3 \leq x+y \leq 4$, and m stands for 0, 1 or 2] are recommended.

As $R^a$, lower alkylcarbonyl(lower alkyl)amino, lower alkylsulfonyl(lower alkyl)amino, lower alkyloxycarbonyl (lower alkyl)amino, and di-lower alkylcarbamoyl(lower alkyl)amino are recommended.

Where m=2, two $R^a$s are independent of each other, while they may together form a group selected from the following:

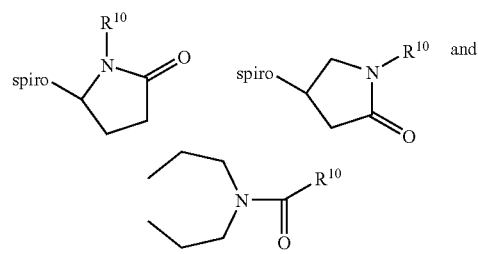

here $R^{10}$ being, for example, lower alkyl, or lower alkylcarbonyl.

Preferred $R^a$ includes methylcarbonyl(methyl)amino, ethylcarbonyl(methyl)amino, ethylcarbonyl(ethyl)amino, isopropylcarbonyl(methyl)amino, isopropylcarbonyl(ethyl) amino, methanesulfonyl(methyl)amino, ethanesulfonyl (methyl)amino, methoxycarbonyl(methyl)amino, ethoxycarbonyl(methyl)amino, 2-pyrrolidinon-1-yl and the like. Preferred $R^{10}$ includes methyl, ethyl, methylcarbonyl, ethylcarbonyl and the like.

As preferred combination of $R^1$ and $R^2$,
- $R^1$: lower alkyl, $R^2$: optionally hydroxyl-substituted lower alkyl
- $R^1$: lower alkyl, $R^2$: tetrahydrofuranyl
- $R^1$: lower alkyl, $R^2$: optionally $R^9$-substituted pyrrolidinyl
- $R^1$: methyl, $R^2$: isopropyl
- $R^1$: methyl, $R^2$: tetrahydrofuranyl
- $R^1$: methyl, $R^2$: N-acetylpyrrolidin-3-yl
- $R^1$: methyl, $R^2$: N-methylpyrrolidon-4-yl
- $R^1$: methyl, $R^2$: N-methylsulfonylpyrrolidin-3-yl and the like are recommended.

As the preferred substituents represented by the formula (A), 1-methyl-2-oxo-1,7-diazaspiro[4.4]nonan-7-yl, 7-methyl-8-oxo-2,7-diazaspiro[4.4]nonan-2-yl, 3-[acetyl(methyl) amino]pyrrolidin-1-yl, 3-[propionyl(methyl)amino]pyrrolidin-1-yl, 3-[isobutyryl(methyl)amino]pyrrolidin-1-yl, 3-[methanesulfonyl(methyl)amino]pyrrolidin-1-yl, 3-[methoxycarbonyl(methyl)amino]pyrrolidin-1-yl, 3-{[(dimethylamino)carbonyl](methyl)amino}pyrrolidin-1-yl, 6-acetyldecahydropyrrolo[3,4-d]azepin-2-yl, 2-oxo[1.3'] bipyrrolidinyl-1'-yl, and the like are recommended.

Of the substituents represented by the formula (A), those particularly preferred are the following:

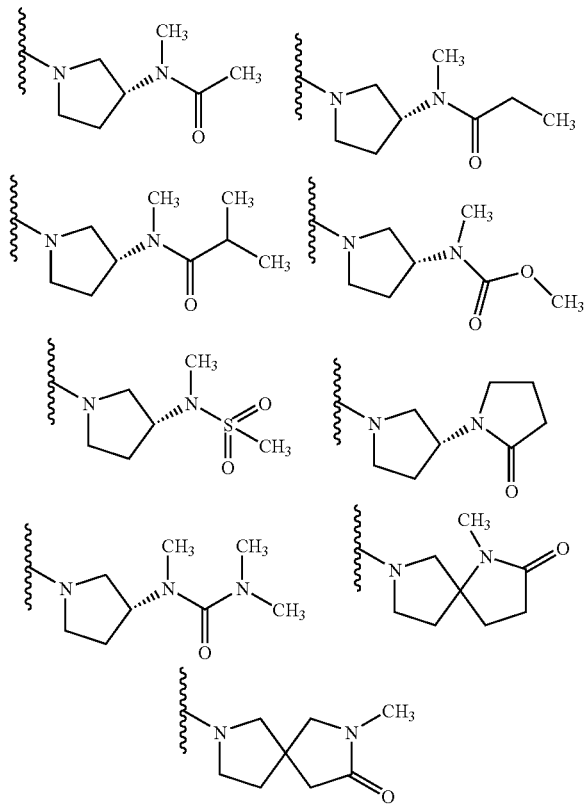

$R^3$, $R^4$, $R^6$ and $R^7$ each independently stands for a substituent selected from the group consisting of
1) hydrogen,
2) hydroxyl,
3) halogen, and
4) optionally halogen-substituted lower alkyl.

As $R^3$, $R^4$, $R^6$ and $R^7$, hydrogen, fluorine, or methyl are preferred, in particular, the case wherein all of them are hydrogen atoms is recommended.

$R^5$ stands for hydrogen or optionally halogen-substituted lower alkyl, preferably hydrogen, methyl or ethyl.

As $R^8$, where n is 2, 3, or 4, each of them independently stands for a substituent selected from the group consisting of
1) halogen,
2) lower alkyl, and
3) lower alkyloxy, preferred examples being fluorine, methyl, ethyl, methoxy, and the like, in particular, fluorine or methoxy.

Preferred n is 0, 1, or 2.

Of the compounds represented by the general formula [I], particularly those represented by a general formula [I-1]

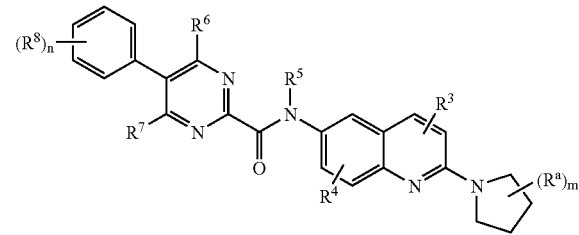

[in which $R^3$, $R^4$, $R^5$, $R^6$, $R^7$, $R^8$, $R^a$, m and n are same as earlier defined] are recommended.

Those compounds represented by the general formula [I-1] exhibit potent MCH-1R antagonistic activity and excel in oral absorption and intracerebral transmigration. They also show high selectivity among other receptors and have excellent effect as medicines.

As specific compounds represented by the general formula [I],
- 5-(4-fluorophenyl)-N-[2-(1-methyl-2-oxo-1,7-diazaspiro [4.4]nonan-7-yl)-6-quinolinyl]-2-pyrimidinecarboxamide,
- 5-(4-fluorophenyl)-N-[2-(7-methyl-8-oxo-2,7-diazaspiro [4.4]-nonan-2-yl)-6-quinolinyl]-2-pyrimidinecarboxamide,
- N-(2-[(3R)-3-[isobutyryl(methyl)amino]-1-pyrrolidinyl]-6-quinolinyl)-5-phenyl-2-pyrimidinecarboxamide,
- N-[2-(6-acetyldecahydropyrrolo[3,4-d]azepin-2-yl)-6-quinolinyl]-5-phenyl-2-pyrimidinecarboxamide,
- N-[2-[(3R)-3-[acetyl(methyl)amino]-1-pyrrolidinyl]-6-quinolinyl)-5-phenyl-2-pyrimidinecarboxamide,
- 5-phenyl-N-(2-[(3R)-3-[propionyl(methyl)amino]-1-pyrrolidinyl]-6-quinolinyl)-2-pyrimidinecarboxamide,
- N-(2-[(3R)-3-[methanesulfonyl(methyl)amino]-1-pyrrolidinyl]-6-quinolinyl)-5-phenyl-2-pyrimidinecarboxamide,
- N-(2-[(3R)-3-[methoxycarbonyl(methyl)amino-1-pyrrolidinyl]-6-quinolinyl)-5-phenyl-2-pyrimidinecarboxamide,
- N-(2-[(3R)-3-[[(dimethylamino)carbonyl)](methyl)amino]-1-pyrrolidinyl]-6-quinolinyl)-5-phenyl-2-pyrimidinecarboxamide,
- N-(2-[isopropyl(methyl)amino]-6-quinolinyl)-5-phenyl-2-pyrimidinecarboxamide,
- 5-(4-fluorophenyl)-N-(2-[(3R)-3-[isobutyryl(methyl) amino]-1-pyrrolidinyl]-6-quinolinyl)-2-pyrimidinecarboxamide,
- N-(2-[(3R)-3-[acetyl(methyl)amino]-1-pyrrolidinyl]-6-quinolinyl)-5-(4-fluorophenyl)-2-pyrimidinecarboxamide,
- 5-(4-fluorophenyl)-N-(2-[methyl(tetrahydro-3-furanyl) amino]-6-quinolinyl)-2-pyrimidinecarboxamide,
- 5-(3-fluorophenyl)-N-(2-[(3R)-3-[isobutyryl(methyl) amino]-1-pyrrolidinyl]-6-quinolinyl)-2-pyrimidinecarboxamide, and the like are recommended.

As the compounds represented by the general formula [I], specific examples are given in Table 1.

TABLE 1

| Example | Formula |
|---|---|
| 1 | |
| 2 | |
| 3 | |
| 4 | |

TABLE 1-continued
| Example | Formula |
|---|---|
| 5 | 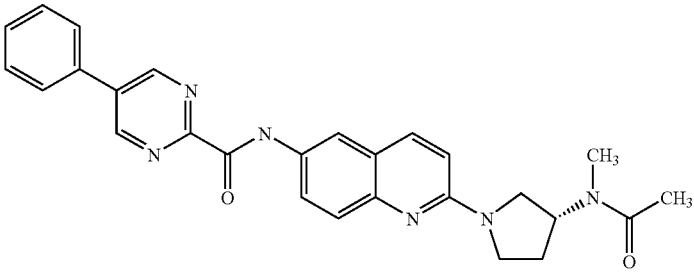 |
| 6 | 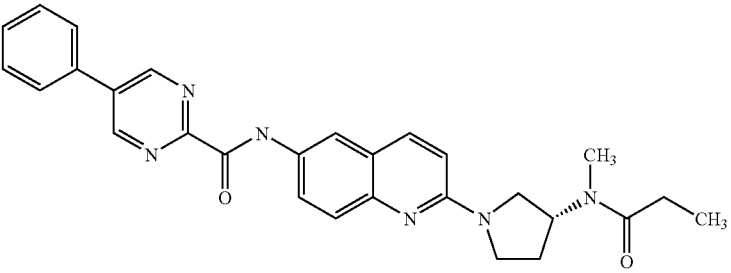 |
| 7 | 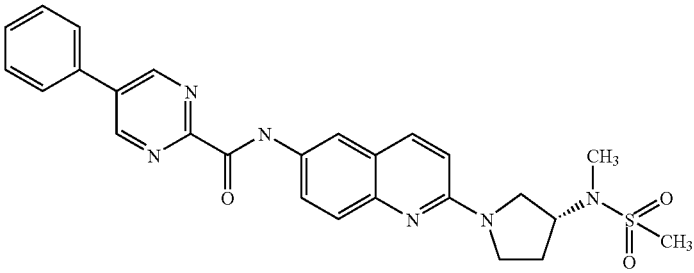 |
| 8 | 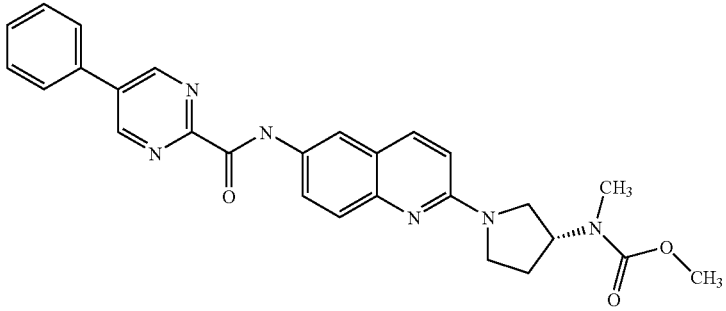 |
| 9 | 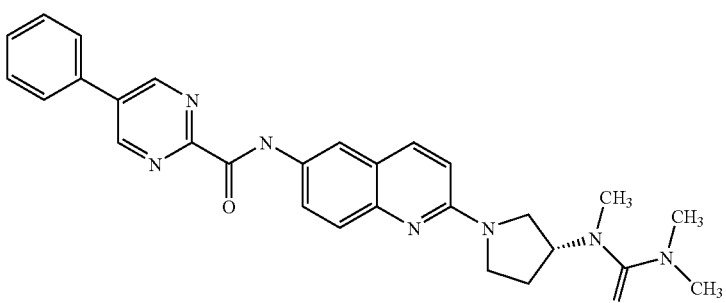 |

TABLE 1-continued

| Example | Formula |
|---|---|
| 10 | |
| 11 | |
| 12 | |
| 13 | |
| 14 | |

Preparation Methods of the Compounds Represented by the General Formula [I]

Those compounds as represented by the general formula [I] can be prepared by, for example, suitably combining the following preparation processes.

Preparation Process 1

Reaction Scheme 1

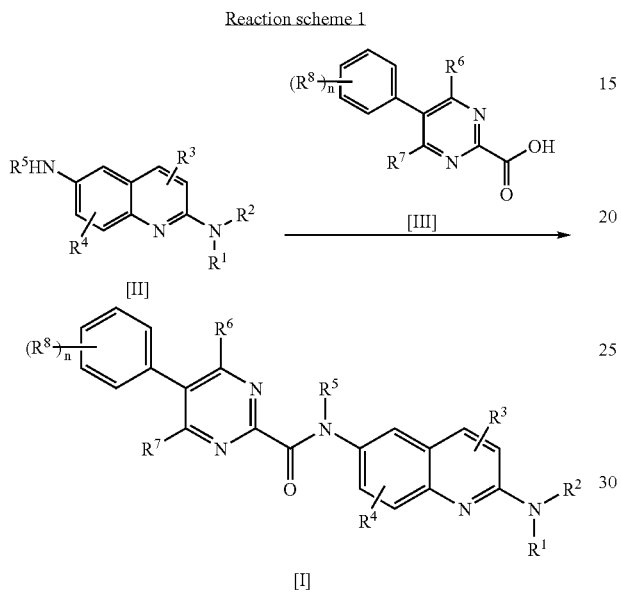

[in which $R^1$, $R^2$, $R^3$, $R^4$, $R^5$, $R^6$, $R^7$, $R^8$ and n are same as earlier defined].

That is, by amidating a compound represented by the general formula [II] and a compound represented by the general formula [III], a compound of the general formula [I] can be obtained.

The amidation can be conducted by per se known methods, for example, one comprising reacting a compound represented by the general formula [II] with a compound represented by the general formula [III] in the presence of a condensing agent, or one comprising activating carboxylic acid moiety of a compound represented by the general formula [III] by a conventionally known means to convert it to a reactive derivative and then amidating said derivative with a compound represented by a general formula [II] (cf. "Fundamentals and Experiments of Peptide Synthesis", Nobuo IZUMIYA, et al., Maruzen Publishing Co., 1983, for both of these methods).

1) Method of Amidation in the Presence of a Condensing Agent

A compound represented by the general formula [II] is amidated with a compound of the general formula [III] in the optional presence of, for example, N-hydroxybenzotriazole (HoBt), using a condensing agent such as 1,3-dicyclohexyl-carbodiimide, 1-ethyl-3-(3-dimethylaminopropyl)-carbodiimide hydrochloride (EDCl) and the like.

The use ratio of the compound of the general formula [III] is, for example, in the range of 0.9-2.0 moles per mole of the compound represented by the general formula [II], in particular, 1.0-1.5 moles being recommended.

Also as the use rate of the condensing agent, 1.0-2.0 moles, preferably 1.0-1.5 moles, per mole of the compound represented by the general formula [III] is recommended.

When HoBt is used, its exemplary use rate can range 0.9-2.0 moles, preferably 1.0-1.2 moles, per mole of the compound represented by the general formula [II].

Furthermore, dimethylaminopyridine may be added to the reaction system for accelerating the reaction, at a use rate of, for example, 0.1-1.0 mole, preferably 0.1-0.5 mole, per mole of the compound represented by the general formula [II].

The amidation reaction is preferably conducted in an organic solvent, examples of suitable solvent including ethers such as 1,4-dioxane ("dioxane"), tetrahydrofuran ("THF"), diethyl ether and the like; aromatic hydrocarbons such as benzene, toluene, xylene, chlorobenzene and the like; halogenated hydrocarbons such as dichloroethane, chloroform, dichloromethane, carbon tetrachloride and the like; pyridine, ethyl acetate, N,N-dimethylformamide ("DMF"), dimethylsulfoxide ("DMSO") and the like.

The reaction temperature may range, for example, 0-80° C., preferably 20-50° C., and the reaction time, 1-48 hours.

2) Method of Amidation Via Reactive Derivative

An object compound is obtained by converting a compound (carboxylic acid) represented by the general formula [III] to a "reactive derivative" by such methods as:
  a) conversion to an acid chloride with a chlorinating agent such as thionyl chloride, oxalyl chloride, phosphorus oxychloride or the like (acid chloride method),
  b) conversion to a mixed acid anhydride using isobutyl chloroformate, methyl chloroformate or the like (mixed acid anhydride method), or
  c) conversion to active esters such as p-nitrophenyl ester, N-hydroxysuccinimide ester or the like (active ester method)

and thereafter subjecting the resulting reactive derivative, either as isolated or without isolation, to an amidation reaction with a compound represented by the general formula [II]. Preparation of such reactive derivatives, furthermore, can be conducted following those methods described in, for example, "Fundamentals and Experiments of Peptide Synthesis" (Nobuo IZUMIYA, et al, Maruzen Publishing Co., 1983).

As the use rate of the reactive derivative, for example, a range of 0.8-3.0 moles, preferably 1.1-1.3 moles, per mole of the compound represented by the general formula [II] is recommended.

This reaction can be accelerated by conducting it in the presence of a basic catalyst. As examples of useful basic catalyst, alkali metal carbonates such as lithium carbonate, sodium carbonate, potassium carbonate and the like; alkali metal hydrogencarbonates such as sodium hydrogencarbonate, potassium hydrogencarbonate and the like; and organic bases such as triethylamine, diisopropylethylamine, tri-n-butylamine, 1.5-diazabicyclo[4.3.0]-5-nonene, 1,8-diazabicyclo[5.4.0]-7-undecene, pyridine, N,N-dimethylaminopyridine and the like can be named.

As use rate of the basic catalyst, for example, 0.1-2.0 moles, preferably 0.1-1.2 moles, per mole of the reactive derivative is recommended.

As the reaction solvent, those named in the above can be used, and as the reaction temperature, for example, −50-80° C., preferably 0-30° C. are recommended. Exemplary reaction time ranges about 30 minutes-24 hours, while preferably 30 minutes-15 hours is recommended.

Also in the amidation reaction using the reactive derivative, dimethylaminopyridine may be used.

Upon extracting and purifying the solution mixture containing a compound represented by the general formula [I] as obtained according to any of the above methods, the compound of the general formula [I] can be isolated.

Production Process 2

Production process 2 is a process for producing the compounds represented by the general formula [II].

Reaction Scheme 2

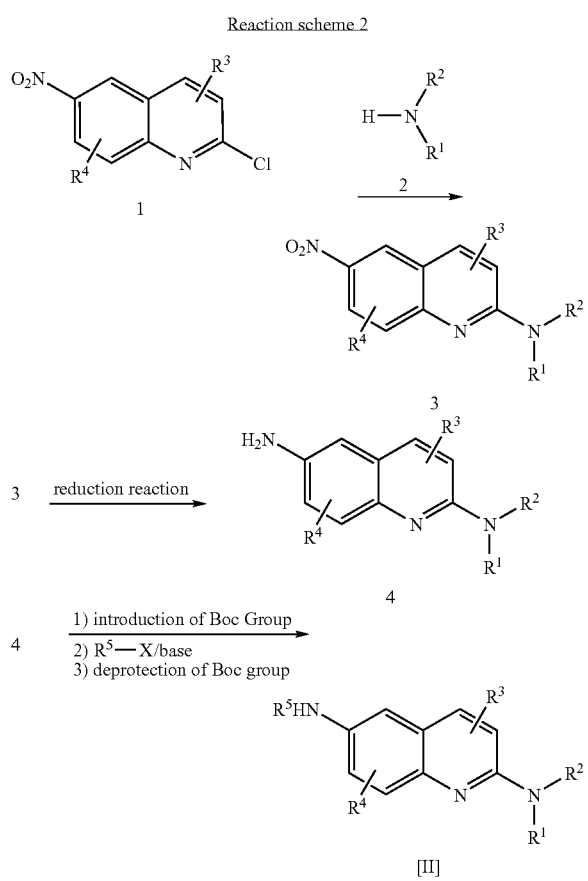

[in which X stands for halogen, trifluoromethanesulfonyloxy and the like; and $R^1$, $R^2$, $R^3$, $R^4$ and $R^5$ are same as earlier defined]

Step 2-1:

Upon heating compound 1 and compound 2 at 20-200° C., preferably 50-150° C., for 10 minutes-48 hours, preferably an hour-24 hours, preferably in the presence of an inert solvent, compound 3 is obtained. This reaction may be conducted in a sealed tube.

Examples of the inert solvent include dioxane, THF, acetonitrile, DMF, DMSO, acetone and the like, among which dioxane, DMF and DMSO are recommended.

As use rate of compound 3, for example, it can be in the range of 1-50 moles per mole of compound 2, in particular, 1-10 moles being recommended.

Then preferably the compound 3 is isolated from the reaction mixture containing the compound 3 and purified by any means known per se, and sent to the next step. Here as the means for isolation and purification, for example, solvent extraction, recrystallization, column chromatography, liquid chromatography, fractionating thin layer chromatography (preparative TLC) and the like can be named. These means are also applicable in the steps hereafter explained.

Step 2-2

Nitro group of compound 3 is reduced to provide compound 4.

As the reduction method, for example, one as described in WO 02/40019 can be used. Where $R^5$ is hydrogen, the compound 4 corresponds to a compound represented by the general formula [II].

Step 2-3

This step is for obtaining a compound represented by the general formula [II], through 1) a step of introducing Boc group into amino group of compound 4 (t-butyloxycarbonylation), 2) a step of reacting the resulting compound with $R^5$—X, in the presence of a base such as NaH, and 3) a step of deprotecting the Boc group of the resulting compound. All of these steps can be carried out by means heretofore known.

Furthermore, compound 1 can be prepared by a known method [*Heterocycles*, Vol. 48, 2637 (1998)] or a method similar thereto. On the other hand, commercially available compounds can be utilized as compound 2, which may also be prepared by those methods as described in Examples in the present specification.

Production Process 3

Production process 3 is for preparing compounds represented by the general formula [III].

Reaction Scheme 3

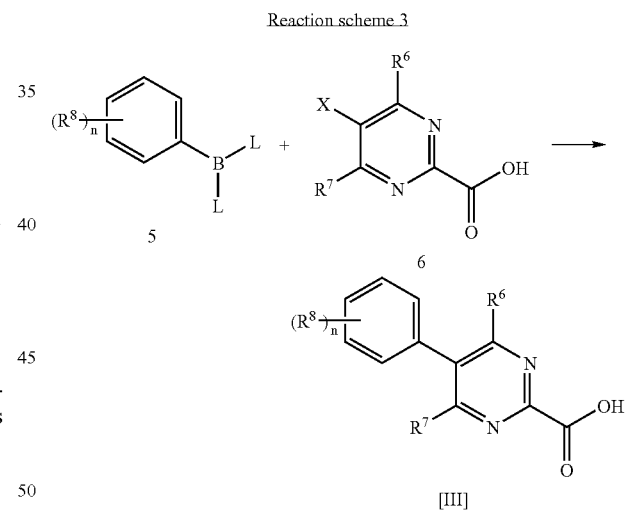

[in which L stands for hydroxyl, lower alkyloxy or the like; X stands for halogen, trifluoromethanesulfonyloxy or the like; and $R^6$, $R^7$, $R^8$ and n are same as earlier defined].

A compound represented by the general formula [III] can be obtained by reacting compound 5 with compound 6 in a solvent, in the presence of palladium catalyst and base. Concerning this reaction (Suzuki coupling), for example, those methods as described in *Tetrahedron*, Vol. 58, 9633 (2002) can be referred to.

As the palladium catalyst, for example, tetrakis-(triphenylphosphine)palladium, palladium acetate, dichlorobis-(triphenylphosphine)palladium, [1,1'-bis(diphenylphosphino)ferrocene]dichloropalladium and the like can be named, and as the base, potassium carbonate, sodium carbonate, potassium phosphate and the like can be named.

As the solvent, alcohols such as t-butanol, ethanol and the like; ethers such as THF, 1,2-dimethoxyethane (DME); aromatic hydrocarbons such as benzene, toluene and the like; or mixed solvents of these are recommended.

Use rate of compound 6 may range 0.9-2.0 moles, preferably 1.0-1.5 moles, per mole of compound 5. As that of the palladium catalyst, it may be, for example, 0.01-0.5 mole per mole of compound 5, and as that of base, 1-5 moles per mole of compound 5.

The reaction temperature can range from room temperature to 150° C., in particular, 70-150° C. being recommended. The reaction time can range normally 1-24 hours.

As compound 5, commercially available chemicals can be used. Also commercially available compound 6 can be used or it may be prepared by known method [e.g., cf. *Journal of Chemical Society*, 3129 (1953)].

In the foregoing Production processes, when such groups as amino, hydroxyl, carboxyl, oxo, carbonyl and the like which do not participate in the reaction are present in the reactant(s), they can be suitably protected with protective groups of amino, hydroxyl, carboxyl, oxo or carbonyl, respectively, before carrying out a reaction of any of Production processes 1-3. After the reactions, the protective groups can be removed.

As "amino-protective group", aralkyl such as benzyl, p-methoxybenzyl, 3,4-dimethoxybenzyl, o-nitrobenzyl, p-nitrobenzyl, benzhydril, trityl and the like; lower alkanoyl such as formyl, acetyl, propionyl, butyryl, pivaloyl and the like; benzoyl; arylalkanoyl such as phenylacetyl, phenoxyacetyl and the like; lower alkyloxycarbonyl such as methoxycarbonyl, ethoxycarbonyl, propyloxycarbonyl, tert-butoxycarbonyl and the like; aralkyloxycarbonyl such as benzyloxycarbonyl, p-nitrobenzyloxycarbonyl, phenethyloxycarbonyl, fluorenylmethoxycarbonyl and the like; lower alkylsilyl such as trimethylsilyl, tert-butyldimethylsilyl and the like; phthaloyl and the like can be named. In particular, acetyl, pivaloyl, benzoyl, ethoxycarbonyl, tert-butoxycarbonyl and phthaloyl are recommended.

As "hydroxyl-protective group", for example, lower alkyl such as methyl, ethyl, propyl, isopropyl, tert-butyl and the like; lower alkylsilyl such as trimethylsilyl, tert-butyldimethylsilyl and the like; lower alkyloxymethyl such as methoxymethyl, 2-methoxyethoxy-methyl and the like; tetrahydropyranyl; trimethylsilylethoxymethyl; aralkyl such as benzyl, p-methoxybenzyl, 2,3-dimethoxybenzyl, o-nitrobenzyl, p-nitrobenzyl, trityl and the like; and acyl such as formyl, acetyl and the like can be named. In particular, methyl, methoxymethyl, tetrahydropyranyl, trityl, trimethylsilylethoxymethyl, tert-butyldimethylsilyl and acetyl are recommended.

As "carboxyl-protective group", for example, lower alkyl such as methyl, ethyl, propyl, isopropyl, tert-butyl and the like; lower haloalkyl such as 2,2,2-trichloroethyl and the like; lower alkenyl such as 2-propenyl; and aralkyl such as benzyl, p-methoxybenzyl, p-nitrobenzyl, benzhydryl, trityl and the like can be named. In particular, methyl, ethyl, tert-butyl, 2-propenyl, benzyl, p-methoxybenzyl and benzhydryl are recommended.

Means for removing protective groups differ depending on kind of the protective groups and stability of individual compounds represented by the general formula [I]. For example, the removal is conducted following those methods described in literature [cf. *Protective Groups in Organic Synthesis*, T. W. Greene, John Wiley & Sons Co., (1981)] or those analogous thereto, by solvolysis using acid or base, i.e., a method of having, for example, from 0.01 mole to a large molar excess of acid, preferably trifluoroacetic acid, formic acid, hydrochloric acid or the like; or from equimolar to a large molar excess of base, preferably potassium hydroxide, calcium hydroxide or the like, act on the object compound; chemical reduction using hydrogenated metal complex or by catalytic reduction using palladium-on-carbon catalyst or Raney nickel catalyst.

Compounds which are obtained by the foregoing methods can be easily isolated and purified by heretofore known separation means. As such means, for example, solvent extraction, recrystallization, column chromatography, liquid chromatography, preparative chromatography and the like can be named.

Compounds of the present invention may have stereoisomers or tautomers such as optical isomers, diastereo isomers, geometrical isomers or the like, depending on the form of their substituents. All of these stereoisomers, tautomers and their mixtures are encompassed by the compounds of the present invention.

Pharmaceutical Compositions Containing the Compounds Represented by the General Formula [I]

Those compounds of the present invention can be administered orally or parenterally, and when formulated into preparation forms adapted for administration, can provide preventing or treating agents for metabolic disorders represented by obesity, diabetes, hormone disorder, hyperlipidemia, gout, fatty liver, hepatitis and cirrhosis; cardiovascular disorders, represented by stenocardia, acute or congestive heart failure, myocardial infarction, coronary atherosclerosis, hypertension, renal diseases and electrolyte abnormality; central nervous system or peripheral nervous system disorders represented by bulimia, emotional disturbance, depression, anxiety, epilepsy, delirium, dementia, schizophrenia, attention-deficit hyperactivity disorder, memory impairment, sleep disorders, cognitive failure, dyskinesia, paresthesias, smell disorders, morphine tolerance, drug dependence and alcoholism; reproductive disorders represented by infertility, preterm labor and sexual dysfunction; digestive disorders; respiratory disorders; cancer or pigmentation. In particular, they are useful as preventing or treating agents for obesity.

In the occasions of clinical use of the compounds of the present invention, the compounds may be formulated into various forms of preparation with addition of pharmaceutically acceptable carriers according to the mode of administration, and thereafter administered. As carriers in such occasions, various additives heretofore known in the field of medical preparations can be used, examples of which include gelatine, lactose, sucrose, titanium dioxide, starch, crystalline cellulose, hydroxypropylmethyl cellulose, carboxymethyl cellulose, corn starch, microcrystalline wax, white petrolatum, magnesium metasilicate aluminate, anhydrous calcium phosphate, citric acid, trisodium citrate, hydroxypropyl cellulose, sorbitol, sorbitan fatty acid ester, polysorbate, sucrose fatty acid ester, polyoxyethylene, hardened castor oil, polyvinylpyrrolidone, magnesium stearate, light silicic anhydride, talc, vegetable oil, benzyl alcohol, gum arabic, propylene glycol, polyalkylene glycol, cyclodextrin or hydroxypropylcyclodextrin and the like.

As the preparation forms formulated as mixtures of these carriers and the compounds of the present invention, for example, solid preparations such as tablet, capsule, granule, powder or suppository; and liquid preparations such as syrup, elixir, or injection and the like can be named, which can be prepared following heretofore known methods in the field of medical preparations. Furthermore, liquid preparations may take such a form as to be dissolved or suspended in water or in other suitable medium immediately before use. Particularly, injections can be dissolved or suspended in physiological saline solution or glucose solution where necessary, and buffer or preservative may further be added thereto.

Those preparations can contain the compounds of the present invention at a rate of 1.0-100% by weight, preferably 1.0-60% by weight, to the whole of individual pharmaceutical preparation; and 0-99.0% by weight, preferably 40-99.0% by weight, of pharmaceutically acceptable carrier. These preparations may also contain therapeutically active other compound(s), for example, treating agents for diabetes, hypertension, arterial sclerosis and the like.

In case of using the compounds of the present invention as preventing or treating agents of said diseases or sicknesses, their dosages and administration frequency differ depending on sex, age, body weight and seriousness of symptoms of individual patients and the kind and scope of intended therapeutic effect. Whereas, generally for oral administration, it is preferred to administer 0.01-400 mg per day per adult patient, as a single dose or several divided doses. For parenteral administration preferably 0.002-100 mg is administered as a single does or several divided doses. Depending on symptoms, preventing administration is permissible.

Combination Therapy

The compounds of the present invention can be used in combination with drugs effective for hypertension, obesity-associated hypertension, hypertension-associated diseases, cardiac hypertrophy, left ventricular hypertrophy, metabolic disorder, obesity, obesity-associated diseases and the like (hereafter referred to as "drug for combined use"). Such drugs can be administered simultaneously, separately or in succession, for prevention or treatment of above-named diseases. When a compound of the present invention is used simultaneously with one, two or more of drugs for combined use, they may be formulated into a medical preparation suited for single administration form. Whereas, for occasions of combination therapy, a composition containing the compound of the present invention and drug(s) for combined use may be administered to the object of medication in different packages, either simultaneously, separately or successively. They may be administered at time interval(s).

Dose(s) of drug(s) for combined use are determinable following clinically adopted dose(s), which can be suitably selected according to individual object of medication, administration route, specific disease, combination of drugs, and the like. Form of administering drug(s) for combined use is not critical but it is sufficient that the compound of the present invention is combined with selected drug(s) for combined use at the time of administration. As adoptable administration forms, for example, 1) administration of single preparation obtained by simultaneously formulating a compound of the present invention and drug(s) for combined use, 2) simultaneous administration of two kinds of preparations obtained by separately formulating a compound of the present invention and drug(s) for combined use, via a same administration route, 3) administration at a certain time interval, via a same administration route, of two kinds of preparations obtained by separately formulating a compound of the present invention and drug(s) for combined use, 4) simultaneous administration of two kinds of preparations obtained by separately formulating a compound of the present invention and drug(s) for combined use, via different administration routes, and 5) administration of two kinds preparations obtained by separately formulating the compound of the present invention and drug(s) for combined use, different administration routes, at a certain time interval (e.g., administration by the order of the compound of the present invention and then the drug(s) for combined use, or by the reversed order) can be adopted. The blend ratio of a compound of the present invention and drug(s) for combined use can be suitably selected, according to individual object of medication, administration route, disease and the like.

As drugs for combined use which can be used in the present invention, for example, those for treating diabetes, hyperlipidemia, hypertension, obesity and the like can be named. Two or more of such drugs for combined use may be combined at an adequate ratio and used.

As drug for treating diabetes, for example, 1) PPAR γ agonists such as glitazones [e.g., ciglitazone, darglitazone, englitazone, isoglitazone (MCC-555) and the like], pioglitazone, rosiglitazone, troglitazone, BRL49653, CLX-0921, 5-BTZD, GW-0207, LG-100641, LY-300512 and the like; 2) biganides such as metformin, buformin, phenformin and the like; 3) protein tyrosine phosphatase-1B inhibitor; 4) sulfonylureas such as acetohexamide, chloropropamide, diabinese, glibenclamide, glipizide, glyburide, glimepiride, gliclazide, glipentide, gliquidone, glisolamide, tolazamide, tolbutamide and the like; 5) meglitinides such as repaglinide, nateglinide and the like; 6) α-glucosidohydroxylase inhibitors such as acarbose, adiposine, camiglibose, emiglitate, miglitol, voglibose, pradimicin-Q, salbostatin, CKD-711, MDL-25,673, MDL-73,945, MOR 14 and the like; 7) α-amylase inhibitors such as tendamistat, trestatin, A1 3688 and the like; 8) insulin secretion promoters such as linogliride, A-4166 and the like; 9) fatty acid oxidation repressors such as clomoxir, etomoxir and the like; 10) A2 antagonists such as midaglizole, isoglidole, deriglidole, idozoxan, earoxan, fluparoxan and the like; 11) insulin or insulin mimetics such as biota, LP-100, novarapid, insulin detemir, insulini lispro, insulin glargine, insulin zinc, Lys-Pro-insulin, GLP-1(73-7), GLP 1 amide (7-36) and the like; 12) non-thiazolidindione such as JT-501, farglitazar and the like; and 13) PPARα/γdual agonists such as MK-0767, CLX-0940, GW-1536, GW-1929, GW-2433, KRP-297, L-796449, LR-90 and SB219994 and the like; can be named.

As said treating agent for hyperlipidemia, for example, 1) cholic acid absorbefacients such as cholestyramine, colesevelem, colestipol, dialkylaminoalkyl derivatives of crossdextran, Colestid™, LoCholest™, Ovestram™ and the like; 2) HMG-CoA reductase inhibitors such as atorvastatin, itavastatin, fluvastatin, lovastatin, pravastatin, rivastatin, rosuvastatin, simvastatin, ZD4522 and the like; 3) HMG-CoA synthesis inhibitors; 4) cholesterol absorption inhibitors such as snatol ester, β-sitosterol, sterol gluoside, ezetimibe and the like; 5) acyl coenzyme A cholesterol acyl transferase inhibitors such as avasimibe, eflucimibe, KY-505, SMP-709 and the like; 6) CETP inhibitors such as JTT 705, torcetrapib, CP532632, BAY-63-2149, SC-591, SC-795 and the like; 7) squalene synthesis inhibitors; 8) antioxidants such as probucol; 9) PPARα agonists such as beclofibrate, benzafibrate, ciprofibrate, clofibrate, ethofibrate, fenofibrate, gemcabene, gemfibrozil, GW-7647, BM-170744, LY-518674, fibric acid derivatives [e.g., Atromid™, Lopid™, Tricor™ and the like; 10) FXR receptor antagonists such as GW-4064, SR-103912 and the like; 11) LXR receptor agonists such as GW3965, T9013137, XTCO-179628 and the like; 12) lipoprotein synthesis inhibitors such as niacin; 13) renin-angiotensin inhibitors; 14) microsome-triglyceride transport inhibitors; 15) cholic acid resorption inhibitors such as BARA 1453, SC435, PHA384640, S-435, AZD7706 and the like; 16) PPAR δ agonists such as GW501516, GW590735 and the like; 17) triglyceride synthesis inhibitors; 18) MTTP inhibitors such as LAB687, CP346086 and the like; 19) low density lipoprotein receptor inducer; 20) squalene epoxidase inhibitors; 21)

thrombocyte agglutination inhibitors; and 22) 5-lipoxygenase-activating protein inhibitors; can be named.

As said treating agents for hypertension, for example, 1) diuretic such as thiazide-type diuretic, e.g., chlorothialidon, chlorothiazide, dichlorophenamide, hydrofluorothiazide, indapamide, hydrochlorothiazide and the like; loop-type diuretic, e.g., bumetanide, ethacrynic acid, furosemide, torsemide and the like; sodium-type diuretic such as amiloride, triamterene and the like; and aldosterone antagonist-type diuretic, e.g., spironolactone, epirenone and the like; 2) β-adrenaline blockers such as acebutolol, atenolol, betaxolol, bevantolol, bisoprolol, bopindolol, carteolol, carvedilol, celiprolol, esmolol, indenolol, metaproplol, nadolol, nebivolol, penbutolol, pindolol, propanolol, sotalol, tertatolol, tilisolol, timolol and the like; 3) calcium channel blockers such as amlodipine, aranidipine, azelnidipine, barnidipine, benidipine, hepridil, cinaldipine, clevidipine, diltiazem, efonidipine, felodipine, gallopamil, isradipine, lacidipine. lemildipine, lercanidipine, nicardipine, nifedipine, nilvadipine, nimodepine, nisoldipine nitrendipine, manidipine, pranidipine, verapamil and the like; 4) angiotensin alteration enzyme inhibitors such as benazepril, captopril, cilazapril, delapril, enalapril, fosinopril, imidapril, losinopril, moexipril quinapril, quinaprilat, ramipril, perindopril, perindropril, quanipril, spirapril, tenocapril, trandolapril, zofenopril and the like; 5) neutral endopeptidase inhibitors such as omapatrilat, cadoxatril, ecadotril, fosidotril, sampatrilat, AVE 7688, ER 4030 and the like; 6) endothelin antagonists such as tezosentan, A308165, YM62899 and the like; 7) vasodilators such as hydrazine, clonidine, minoxidil, nicotinyl alcohol and the like; 8) angiotension II antagonists such as candesartan, eprosartan, irbesartan, losartan, pratosartan, tasosartan, telmisartan, valsartan, EXP-3137, FI6828K, RNH6270 and the like; 9) α/β adrenaline blockers such as nipradilol, arotinolol, amosulalol and the like; 10) α1 blockers such as terazosin, urapidil, prazosin, bunazosin, trimazosin, doxazosin, naftopidil, indoramin, WHIP164, XEN010 and the like; 11) α2 agonists such as lofexidine, tiamenidine, moxonidine, rilmenidine, guanobenz and the like; and 12) aldosteron inhibitors can be named.

As said anti-obesity agents, for example, 1) 5HT (serotonin) transporter inhibitors such as paroxetine, fluoxetine, fenfluramine, fluvoxamine, sertraline, imipramine and the like; 2) norepinephrine transporter inhibitors such as GW320659, desipramine, talsupram, nomifensine and the like; 3) cannabinoid 1 receptor 1 (CB-1) antagonist/inverse agonist such as rimonabant (Sanofi Synthelabo), SR-147778 (Sanofi Synthelabo), BAY-65-2520 (Bayer), SLV-319 (Sorbay) and those compounds disclosed in U.S. Pat. Nos. 5,532,237, 4,973,587, 5,013,837, 5,081,122, 5,112,820, 5,292,736, 5,624,941, 6,028,084, WO96/33159, WO98/33765, WO98/43636, WO98/43635, WO01/09120, WO01/96330, WO98/31227, WO98/41519, WO98/37061, WO00/10967, WO00/10968, WO97/29079, WO99/02499, WO01/58869, WO02/076949, WO01/64632, WO01/64633, WO01/64634, WO03/006007, WO03/007887 and EP-658546, and the like; 4) ghrelin antagonists such as those compounds disclosed in, e.g., WO01/87355 and WO02/08250; 5) histamine (H3) antagonist/inverse agonist such as thioperamide, 3-(1H imidazol-4-yl)propyl N-(pentenyl)carbonate, clobenpropit, iodophenpropit, imoproxifan, GT2395, A331440, compounds disclosed in WO02/15905, 0-[3-(1H-imidazo-4-yl)propanol] carbamate, piperazin-containing H3 receptor antagonist (Lazewska, D. et al., Pharmazie, 56:927-32 (2001), benzophenone derivatives (Sasse, A. et al., Arch. Pharm. (Weinheim) 334:45-52 (2001)) substituted N-phenylcarbamate (Reidemeister, S. et al., Pharmazie, 55:83-6(2000)), proxyphene derivatives (Sasse, A. et al., J. Med. Chem. 43:3335-43(2000)) and the like; 6)MCH-1R antagonists such as T-226296(Takeda), SNAP-7941(Synaptic) and other compounds disclosed in WO01/82925, WO01/87834, WO02/051809, WO02/06245, WO02/076929, WO02/076947, WO02/04433, WO02/51809, WO02/083134, WO02/094799, WO03/004027 and JP2001-226269A, and the like; 7) MCH-2R agonist/antagonists; 8) NPY1 antagonists such as 3-chloro-5-(1-(6-[2-(5-ethyl-4-methyl-thiazol-2-yl)-ethyl]-4-morpholinyl-4-yl-pyridin-2-ylamino)-ethyl)phenyl] carbamic acid isopropyl ester, BIBP3226, BIB03304, LY-357897, CP-671906, GI-264879, and other compounds disclosed in USP6001836, WO96/14307, WO01/23387, WO99/51600, WO01/85690, WO01/85098, WO01/85173 and WO01/89528, and the like; 9) NPY5 antagonists such as L-152804, GW-569180A, GW-594884A, GW-587081X, GW-548118X, FR235,208, FR226928, FR240662, FR252384, 1229U91, GI-264879A, CGP71683A, LY-377897, LY366377, PD-160170, SR-120562A, SR-120819A, JCF-104, H409/22, and other compounds disclosed in U.S. Pat. Nos. 6,140,354, 6,191,160, 6,258,837, 6,313,298, 6,337,332, 6,329,395, 340,683, 6,326,375, 6,329, 395, 6,337,332, 6,335,345, EP-01010691, EP-01044970, WO97/19682, WO97/20820, WO97/20821, WO97/20822, WO97/20823, WO98/27063, WO00/107409, WO00/185714, WO00/185730, WO00/64880, WO00/68197, WO00/69849, WO01/09120, WO01/14376, WO01/85714, WO1/85730, WO01/07409, WO01/02379, WO01/02379, WO01/23388, WO01/23389, WO01/44201, WO01/62737, WO01/62738, WO01/09120, WO02/20488, WO02/22592, WO02/48152, WO02/49648, WO02/094789 and Norman et al., J. Med. Chem. 43:4288-4312 (2000), and the like; 10) leptins such as human recombinant leptin (PEG-OB, Hoffman La Roche), recombinant methionyl-leptin (Amgen) and the like; 11) leptin derivatives such as those compounds which are disclosed in U.S. Pat. Nos. 5,552,524, 5,552,523, 5,552,522, 5,521,283, WO96/23513, WO96/23514, WO96/23515, WO96/23516, WO96/23517, WO96/23518, WO96/23519 and WO96/23520, and the like; 12) opioid antagonists such as Nalmefene (registered trademark to Revex), 3-methoxynaltrexone, naloxone, naltrexone, compounds disclosed in WO00/21509 and the like; 13) orexin antagonists such as SB-334867A and other compounds disclosed in WO01/96302, WO01/68609, WO02/51232, WO02/51838, WO03/023561, and the like; 14) bombesin receptor subtype 3 agonist; 15) cholecystolinin A (CCK-A) agonists such as AR-R15849, GI-181771, JMV-180, A-71378, A-71623, SR-146131, other compounds disclosed in USP-5739106, and the like; 16) CNTF (ciliary neurotrophic factors) such as GI-181771 (Glaxo-SmithKline), SR146131 (Sanofi Synthelabo), butabindide, PD170,292, PD149164 (Pfizer) and the like; 17) CNTF derivatives such as axokine (Regeneron), other compounds which are disclosed in WO94/09134, WO98/22128 and WO99/43813, and the like; 18) growth hormone secretion receptor agonists such as NN 703, hexarelin, MK-0677, SM-130686, CP-424,391, L-692,429, L-163, 255, U.S. Pat. No. 6,358,951,U.S. Patent Application Nos. 2002/049196 and 2002/022637, WO01/56592 and WO02/32888, and the like; 19) serotonin receptor 2C agonists such as BVT933, DPCA37215, IK264, PNU22394, WAY161503, R-1065, YM348, other compounds disclosed in U.S. Pat. No. 3,914,250, WO02/36596, WO02/48124, WO02/10169, WO01/66548, WO02/44152, WO02/51844, WO02/40456 and WO02/40457, and the like; 20) melanocortin 3 receptor agonist; 21) melanocortin 4 receptor agonists such as CHIR86036 (Chiron), ME-10142, ME-10145 (Melacure), other compounds disclosed in WO99/64002, WO00/74679, WO01/991752, WO01/74844, WO01/70708, WO01/70337, WO01/91752, WO02/059095, WO02/059107, WO02/059108, WO02/059117, WO02/12166, WO02/11715, WO02/12178, WO02/15909, WO02/068387, WO02/068388, WO02/067869, WO03/007949 and WO03/009847, and the like; 22) monoamine resorption inhibitors such as Sibutramine (registered trademark to Meridia/Reductil) and salts thereof, other derivatives disclosed in U.S. Pat. Nos. 4,746,680 4,806,570, 5,436,272, US Patent Application No. 2002/0006964, WO01/27068 and WO01/62341, and the like; 23) monoamine re-introjection inhibitors such as dexfenfluramine, fluoxetine, other compounds disclosed in U.S. Pat. No. 6,365,633, WO01/27060 and WO01/162341, and the like; 24) glucagons-like peptide 1 agonist; 25) Topiramate (registered trademark to Topimax); 26) phytopharm compound 57 (e.g., CP644,673); 27)acetyl CoA carboxylase 2 (ACC2) inhibitor; 28) β-adrenalin receptor 3 agonists such as AD9677/TAK677(Dainippon Pharmaceutical/Fakeda Pharmaceutical), CL-316,243, SB418790, BRL-37344, L-796568, BMS-196085, BRL-35135A, CGPI2177A, BTA-243, W427353, Trecadrine, ZenecaD7114, SR59119A, other compounds disclosed in U.S. Pat. Nos. 5,705,515, 5,451,677, WO01/74782 and WO02/32897, and the like; 29) diacylglycerolacyl transferase 1 inhibitor; 30) diacylglycerolacyl transferase 2 inhibitor; 31) fatty acid synthesis inhibitors such as Cerulenin, C75 and the like; 32) phosphodiesterase inhibitors such as theofylline pentoxyfylline, zaprinast, sildenafil, amrinone, milrinone, cilostamide, rolipram, cilomilast and the like; 32) thyroid hormone P agonists such as KB-2611 (KaroBio BMS), other compounds disclosed in WO02/15845 and JP2000-256190A, and the like; 33) phytanic acid such as phytanic acid, 4-[(E)-2-(5,6,7,8-tetrahydro-5,5,8,8-tetramethyl-2-naphthalenyl)-1-propenyl] benzoic acid (TTNPB), retinoic acid, other compounds disclosed in WO99/00123, and the like; 34) acyl estrogens such as oleoylestrone, compounds disclosed in del Mar-Grasa, M. et al., Obesity Reseach, 9: 202-9 (2001); 35) glucocorticoid antagonist; 36) 11-β hydroxysteroid dehydrognase 1-type inhibitors such as BVT 3498, BVT 2733, other compounds disclosed in WO01/90091, WO 01/90090 and WO01/90092, and the like; 37) stearyl-CoA desaturase 1 inhibitors; 38) dipeptidyl peptidase IV inhibitors such as isoleucine thiazolidide, valine pyrrolidide, NVP-DPP728 AF237, P93/01, TSL225, TMC-2A/2B/2C, FE999011, P9310/K364, VIP177, SDZ274444, other compounds disclosed in WO03/004498, WO03/004496, EP1258476, WO02/083128, WO02/062764, WO03/000250, WO03/002530, WO03/002531, WO03/002553, WO03/002593, WO03/000180 and WO03/000181, and the like; 39) lipase inhibitors such as Tetrahydro lipstatin (registered trademark to Orlistat/Xenical), Triton WR 1339, RHC 80267, lipstatin, tea saponin, diethylumbelliferyl phosphate, FL-386, WAY-121898, BAY-N-3176, valilactone, esteracin, ebelactone A, ebelectone B, RHC80267, other compounds disclosed in WO01/77094, U.S. Pat. No. 4,598,089, U.S. Pat. No. 4,452,813, U.S. Pat. No. 5,512,565, U.S. Pat. No. 5,391,571, U.S. Pat. No. 5,602,151, U.S. Pat. No. 4,405,644, U.S. Pat. No. 4,189,438 and U.S. Pat. No. 4,242,453, and the like; 39) fatty acid transporter inhibitors; 40) dicarboxylate transporter inhibitors; 41) glucose transporter inhibitors; 42) phosphate transporter inhibitors; and the like can be named.

Those combination drugs are obtained by concurrent use of a compound of the present invention with one, two, or more of above drugs for combined use. Furthermore, said combination drugs are useful for prevention or therapy of metabolic disorders, when combined with one, two or more drugs selected from the group consisting of diabetes-treating agents and hyperlipidemia-treating agents. Combinations containing, in particular, hypertension-treating agent and antiobesity agent are useful for prevention or therapy of metabolic disorders with synergistic effect, when diabetes-treating agent(s) and/or hyperlipidemia-treating agent(s) are added thereto.

BRIEF EXPLANATION OF DRAWING

To rats satiated with high fat diet, compounds of the present invention were orally administered, and an hour after the administration, MCH was intraventricularly administered. The rats' feed intakes during the following two hours are shown in FIG. 1.

BEST MODE FOR CARRYING OUT THE INVENTION

Figure 1:
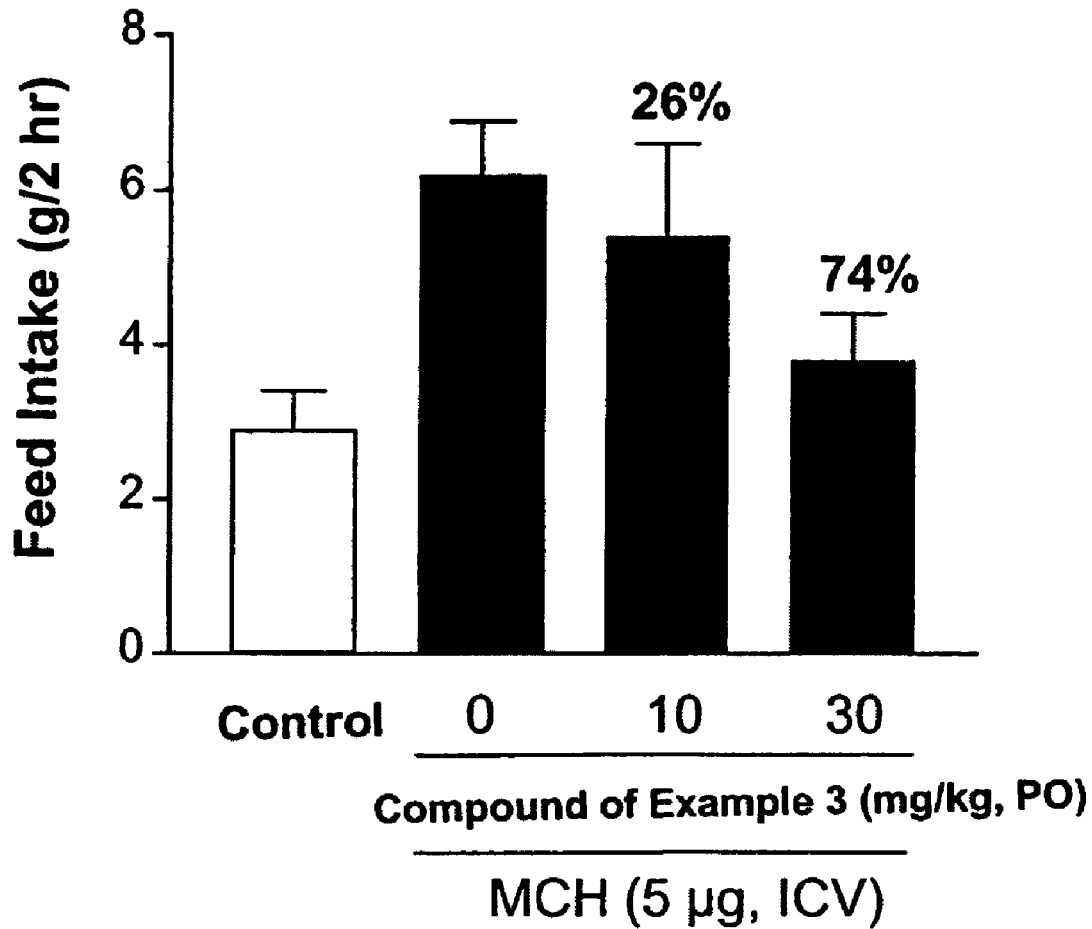

Hereinafter the present invention is explained in detail referring to working Examples, it being understood that the invention is in no sense limited by said Examples. Those reagents used in the Examples were commercially available chemicals, unless otherwise specified. Mass spectra were measured by Electro Spray Ionization Method (ESI).

REFERENTIAL EXAMPLE 1

1-Methyl-7-(6-nitro-2-quinolinyl)-2-oxo-1, 7-diazaspiro[4,4]-nonane (1) To a solution of diisopropylamine (12 ml) in THF (200 ml), n-butyl lithium (2.6 M-hexane solution, 32 ml) was added under cooling with ice, followed by 20 minutes' stirring at the same temperature. The solution was then cooled to −78° C. and into which a THF solution (30 ml) of 1-(tert-butyl)3-methyl 1,3-pyrrolidine-dicarboxylate (13.0 g) was added dropwise, followed by an hour's stirring at the same temperature. Then allyl bromide (10 ml) was added to the reaction liquid, followed by an hour's stirring at −78° C. and another hour's stirring at room temperature. Saturated aqueous ammonium chloride solution was added to the reaction liquid which was subsequently extracted with ethyl acetate. The resulting ethyl acetate layer was dried over anhydrous sodium sulfate and concentrated under reduced pressure. The residue was subjected to column chromatography (hexane:ethyl acetate=15:1) to provide 1-(tert-butyl)3-methyl 3-allyl-1,3-pyrrolidinedicarboxylate (13.3 g) as a yellow oily substance.

(2) To a THF-methanol (50 ml-50 ml) solution of the compound as obtained in (1) (13.3 g, 40 mmol), 4N aqueous sodium hydroxide solution (20 ml) was added and stirred at 50° C. for an hour. The reaction liquid was neutralized with 5N aqueous hydrochloric acid, extracted with chloroform, dried over anhydrous sodium sulfate and concentrated under reduced pressure. The resulting residue was dissolved in toluene (100 ml) and to which phenylphosphoryl-azide (13.5 g) and triethylamine (6.9 ml) were added, followed by an hour's stirring at 80° C. Successively benzyl alcohol (6.6 ml) was added to the reaction liquid and stirred an overnight at 100° C. The reaction liquid was distilled under reduced pressure and the resulting residue was subjected to column chromatography (hexane:ethyl acetate=6:1) to provide tertbutyl 3-allyl-3-[(benzyloxy)carbonyl]-amino-1-pyrrolidinecarboxylate (13.0 g) as a colorless oily substance.

(3) To a THF (130 ml) solution of the compound as obtained in (2) (10.2 g), 9-BBN (2M-THF solution, 113 ml) was added under cooling with ice, followed by an overnight stirring at room temperature. Further, methanol (2 ml), 3N aqueous sodium hydroxide solution (20 ml) and 30% aqueous hydrogen peroxide were added to the reaction liquid by the order stated, under cooling with ice followed by 3 hours' stirring at room temperature. Successively saturated aqueous sodium hydrogencarbonate solution was added to the reaction liquid, followed by extraction with diethyl ether. The diethyl ether layer was dried over anhydrous sodium sulfate and concentrated under reduced pressure. The resulting residue was subjected to column chromatography (hexane:ethyl acetate=3:2) to provide tert-butyl 3-[(benzyloxy)carbonyl] amino-3-(3-hydroxypropyl)-1-pyrrolidinecarboxylate (7.9 g) as a colorless oily substance.

(4) To a DMF (30 ml) solution of the compound as obtained in (3) (3.2 g), imidazole (860 mg) and tert-butyldimethylchlorosilane (1.5 g) were added under cooling with ice, followed by 4 hours' stirring at room temperature. Water was added to the reaction liquid which was then extracted with ethyl acetate, and the ethyl acetate layer was dried over anhydrous sodium sulfate and concentrated under reduced pressure. The residue was dissolved in DMF (30 ml), and to the solution sodium hydride (60% oily substance, 500 mg) was added under cooling with ice, followed by an hour's stirring at the same temperature. Further methane iodide (1.3 ml) was added to the reaction liquid and stirred for 2 hours at room temperature. The reaction liquid was poured into water, to which saturated aqueous ammonium chloride solution was added, followed by extraction with ethyl acetate. The ethyl acetate layer was dried over anhydrous sodium sulfate and concentrated under reduced pressure. To the residue tetrabutylammonium fluoride (1M-THF solution, 15 ml) was added, followed by an hour's stirring at room temperature. Saturated aqueous ammonium chloride solution was further added to the reaction liquid, followed by extraction with ethyl acetate and the resulting ethyl acetate layer was dried over anhydrous sodium sulfate and concentrated under reduced pressure. The residue was subjected to column chromatography (hexane: ethyl acetate=3:2) to provide tert-butyl 3-[[(benzyloxy)carbonyl](methyl)amino]-3-(3-hydroxypropyl)-1-pyrrolidinecarboxylate (3.4 g) as a colorless oily substance.

(5) A methylene chloride (100 ml) solution of oxalyl chloride (1.5 ml) was cooled to −78° C., to which DMSO (1.5 ml) was added, followed by 30 minutes' stirring at the same temperature. Successively a methylene chloride (15 ml) solution of the compound as obtained in (4) (3.4 g) was added to the solution dropwise, followed by addition of triethylamine (7 ml) and an hour's stirring at room temperature. Saturated aqueous ammonium chloride solution was added to the reaction liquid, followed by extraction with ethyl acetate and the resulting ethyl acetate layer was dried over anhydrous sodium sulfate and concentrated under reduced pressure. The residue was dissolved in aqueous tert-butanol solution (75%, 200 ml), and to the solution 2-methyl-2-butene (4.5 ml), sodium dihydrogenphosphate (2.0 g) and sodium chlorite (2.8 g) were added under cooling with ice, by the order stated, followed by an hour's stirring at room temperature. Saturated aqueous ammonium chloride solution was added to the reaction liquid, followed by extraction with ethyl acetate and the resulting ethyl acetate layer was dried over anhydrous sodium sulfate and concentrated under reduced pressure. The residue was dissolved in methanol (30 ml), and to which solution trimethylsilyldiazomethane-hexane solution (2M-hexane solution, 20 ml) was added, followed by 30 minutes' stirring at room temperature. After distilling the reaction liquid at reduced pressure, the residue was subjected to column chromatography (hexane:ethyl acetate=5:1) to provide tert-butyl 3-([(benzyloxy)carbonyl](methyl)amino)-3-(3-methoxy-3-oxopropyl)-1-pyrrolidinecarboxylate (3.2 g) as a colorless oily substance.

(6) To a methanol (30 ml) solution of the compound as obtained in (5) (1.0 g), palladium hydroxide (200 mg) was added and stirred for 2 hours at room temperature in hydrogen atmosphere. The reaction liquid was filtered, the solvent was distilled off under reduced pressure and toluene (60 ml) was added to the resulting residue, followed by 2 hours' stirring at 100° C. Distilling the toluene off under reduced pressure, 4N-hydrochloric acid-dioxane solution (20 ml) was added and stirred for 2 hours at room temperature. Distilling the reaction liquid at reduced pressure, 2-chloro-6-nitroquinoline (620 mg), potassium carbonate (830 mg) and isopropanol (20 ml) were added to the residue and the resulting mixture was stirred an overnight at 100° C. Water was added to the reaction liquid which then was extracted with ethyl acetate. The ethyl acetate layer was dried over anhydrous sodium sulfate and concentrated under reduced pressure. The residue was subjected to column chromatography (ethyl acetate) to provide the title compound (740 mg) as a yellow solid. ESI-MS Found: m/z 327 [M+H]+

REFERENTIAL EXAMPLE 2

7-Methyl-2-(6-nitro-2-quinolinyl)-8-oxo-2,7-diaza-spiro[4,4]-nonane (1) A solution of 3-pyrrolidinol (4.0 g) in dioxane-water (10:1, 50 ml) mixed solvent was cooled to 5° C., and into which a solution of 4-nitrobenzyl chloroformate (10.9 g) in dioxane (20 ml) was added dropwise, while maintaining the pH at 8-9, followed by 10 minutes' stirring at 5° C. Distilling the solvent off under reduced pressure, the residue was extracted with ethyl acetate. The organic layer was dried over anhydrous magnesium sulfate, and from which the solvent was distilled off under reduced pressure. Washing the residue with ethyl acetate, 3-hydroxy-1-(p-nitrobenzyloxycarbonyl) pyrrolidine (6.6 g) was obtained as a pale yellow solid.

(2) A solution of the compound as obtained in (1) (6.3 g) and triethylamine (26.5 ml) in DMSO (76 ml) was cooled to 110° C., to which pyridine sulfur trioxide complex (11.3 g) was added. After stirring the system an overnight at room temperature, water was added to the reaction liquid and extracted with dichloromethane. The organic layer was dried over anhydrous magnesium sulfate and the solvent was distilled off under reduced pressure. Subjecting the resulting residue to silica gel column chromatography (hexane:ethyl acetate=3:2-2:3), 1-(p-nitrobenzyloxycarbonyl)-3-pyrrolidinone (4.5 g) was obtained.

1H-NMR(300 MHz,CDCl$_3$,δppm):2.65(2H,m), 3.88(4H, m), 5.24(2H,s), 7.53(2H,d,J=7.5 Hz),8.22(2H,d,J=7.5 Hz).

(3) Sodium hydride (60% oily substance, 1.6 g) was suspended in THF (50 ml) and cooled to 0° C. Into the suspension a solution of triethyl phosphonoacetate (9.7 g) in THF (10 ml) was added dropwise, at temperatures not higher than 10° C., followed by 30 minutes' stirring at 0-5° C. Into the reaction liquid a solution of the compound as obtained in above (2) (3.5 g) in THF (10 ml) was added dropwise to 110° C. or below. After the following stirring for 4 hours at room temperature, water was added to the reaction liquid which was then distilled under reduced pressure. The residue was extracted with ethyl acetate and washed with saturated saline. The organic layer was dried over anhydrous magnesium sulfate, and the solvent was distilled off under reduced pressure. Subjecting the resulting residue to silica gel column chromatography (hexane:ethyl acetate=4:1-3:2), p-nitrobenzyl 3-(2-methoxy-2-oxoethyl)-3-(nitromethyl)-1-pyrrolidinecarboxylate (4.2 g) was obtained.

1H-NMR(300 MHz,CDCl$_3$,δppm): 1.28(3H,t,J=7.5 Hz), 2.73(1H,m), 3.19(2H,m), 3.65(1H,m), 4.14(2H,q,J=7.5 Hz), 4.21(2H,brs), 5.21(2H,s), 5.67(1H,m), 7.52(2H,d,J=7.5 Hz), 8.22(2H,d,J=7.5 Hz).

(4) To a solution of the compound as obtained in (3) (3.9 g) in nitromethane (160 ml), 1,1,3,3-tetramethylguanidine (0.8 ml) was added and refluxed under heating an overnight. The reaction liquid was concentrated under reduced pressure, and the resulting residue was subjected to silica gel column chromatography (hexane:ethyl acetate=4:1-3:2) to provide p-nitrobenzyl 3-(2-methoxy-2-oxoethyl)-3-(nitromethyl)-1-pyrrolidinecarboxylate (1.37 g).

1H-NMR(300 MHz,CDCl$_3$,δppm): 1.28(3H,t,J=7.5 Hz), 2.04(2H,m), 2.63(2H,m), 3.60(4H,m), 4.18(2H,q,J=7.5 Hz), 4.70(2H,m), 5.21(2H,s), 7.51(2H,d,J=7.5 Hz), 8.22(2H,d, J=7.5 Hz).

(5) To a 50% aqueous methanol solution (80 ml) of the compound obtained in (4) above (500 mg), iron powder (425 mg) and ammonium chloride (815 mg) were added, and heated under reflux for 50 minutes. The reaction liquid was cooled to room temperature and filtered with Celite®. The filtrate was concentrated under reduced pressure, to which acetone (20 ml) was added, and the supernatant was removed by decantation. DMF (20 ml) was added to the residue and filtered through Celite®. Concentrating the filtrate under reduced pressure, 3-oxo-2,7-diazaspiro[4,4]nonane was obtained, which was used in the next step without purification.

(6) To a solution of the compound as obtained in (5) in DMF (10 ml), 2-chloro-6-nitroquinoline (250 mg) and potassium carbonate (248 mg) were added, and stirred an overnight at 90° C. Distilling the solvent off under reduced pressure, the resulting residue was subjected to silica gel column chromatography (chloroform:methanol=10:1) to provide 2-(6-nitro-2-quinolinyl)-8-oxo-2,7-diazaspiro[4,4]-nonane (44 mg).
1H-NMR(300 MHz,CDCl$_3$,δppm):2.17(1H,d,J=8.3 Hz), 2.21(1H,d,J=8.3 Hz), 2.43(1H,d,J=15 Hz), 2.51(1H,d,J=15 Hz), 3.41(1H,d,J=11 Hz), 3.47(1H,d,J=11 Hz), 3.73(4H,m), 6.82(1H,d,J=8.2 Hz), 7.68(1H,d,J=9.0 Hz), 7.97(1H,d,J=9.0 Hz), 8.31(1H,dd,J=8.2,2.2 Hz), 8.55(1H,d,J=2.2 Hz). ESI-MS Found:m/z 313[M+H]+

(7) To a solution of the compound as obtained in (6) (44 mg) in DMF (4 ml), sodium hydride (60% oily substance, 17 mg) was added under gaseous nitrogen stream, followed by 25 minutes' stirring at room temperature. To the reaction liquid a solution of methyl iodide (99 mg) in DMF (1 ml) was added and stirred for 30 minutes. Water was successively added to the reaction liquid which then was extracted with chloroform-methanol (10:1) mixed solvent. The organic layer was dried over anhydrous magnesium sulfate, and the solvent was distilled off under reduced pressure. The resulting residue was subjected to preparative TLC (chloroform: methanol=10:1) to provide the title compound (27 mg).

1H-NMR(300 MHz,CDCl$_3$,δppm):2.14(1H,d,J=8.3 Hz), 2.18(1H,d,J=8.3 Hz), 2.49(1H,d,J=15 Hz), 2.56(1H,d,J=15 Hz), 2.81(3H,s), 3.39(1H,d,J=11 Hz), 3.55(1H,d,J=11 Hz), 3.75(4H,m), 6.79(1H,d,J=8.2 Hz), 7.65(1H,d,J=9.0 Hz), 7.95 (1H,d,J=9.0 Hz), 8.28(1H,dd,J=8.2,2.2 Hz), 8.51(1H,d,J=2.2 Hz). ESI-MS Found:m/z 327[M+H]+

REFERENTIAL EXAMPLE 3

(3R)-N-methyl-N-[1-(6-nitro-2-quinolinyl)-3-pyrrolidinyl]-isobutylamide (1) To a solution of (3R)-(–)-1-benzyl-3-(methylamino)-pyrrolidine (20.0 g) in tetrahydrofuran (200 ml), triethylamine (29.3 ml) and di-tert-butyl-dicarbonate (34.4 g) were added at 0° C., followed by stirring an overnight at room temperature. Water was added to the reaction liquid which then was extracted with diethyl ether. The organic layer was washed with saturated saline, dried over anhydrous sodium sulfate, and concentrated under reduced pressure. To the residue 4N hydrochloric acid-ethyl acetate solution (29.0 ml) was added, and formed white crystals were washed with diisopropyl ether, and filtered. Drying the product, tert-butyl (3R)-N-(1-benzyl-3-pyrrolidinyl)-N-methylcarbamate hydrochloride (24.2 g) was obtained as white crystals. ESI-MS Found: m/z 235[M+H]+

(2) To a solution of the compound as obtained in above (1) (22.0 g) in methanol (225 ml), 10% palladium-on-carbon (7.2 g) was added in gaseous nitrogen atmosphere, followed by an overnight stirring under one atmospheric hydrogen atmosphere. The reaction was suspended by nitrogen-exchanging the reaction system, and the reaction liquid was filtered through Celite® and concentrated under reduced pressure. Drying the product, tert-butyl (3R)-N-methyl-N-(3-pyrrolidinyl)carbamate hydrochloride (15.9 g) was obtained as white crystals. ESI-MS Found:m/z 201[M+H]+

(3) To a solution of 2-chloro-6-nitroaminoquinoline (7.13 g) in DMF (110 ml), potassium carbonate (14.2 g) and the compound as obtained in above (2) (8.90 g) were added, and stirred an overnight at 90° C. To the reaction liquid water (400 ml) was added and the formed crystals were recovered by filtration. The product was dried to provide tert-butyl (3R)-N-methyl-N-[1-(6-nitro-2-quinolinyl)-3-pyrrolidinyl]carbamate (11.4 g) as yellow crystals. ESI-MS Found:m/z 273 [M+H]+

(4) The compound as obtained in above (3) (11.2 g) was dissolved in trifluoroacetic acid (110 ml) and stirred for 20 minutes. The reaction liquid was concentrated under reduced pressure, and to the residue 2N aqueous sodium hydroxide solution was added, followed by extraction with chloroform. The organic layer was washed with saturated saline, dried over anhydrous sodium sulfate and concentrated under reduced pressure. To a solution of the resulting residue in chloroform (60 ml), triethylamine (8.4 ml) and isobutyryl chloride (3.8 ml) were added and stirred for an hour. Aqueous sodium hydrogencarbonate solution was added to the reaction liquid which then was extracted with chloroforom. The organic layer was washed with saturated saline, dried over anhydrous sodium sulfate and concentrated under reduced pressure. The residue was subjected to silica gel column chromatography (chloroforom: methanol=95:5) to provide the title compound (10.3 g) as yellow crystals. ESI-MS Found:m/z 243[M+H]+

REFERENTIAL EXAMPLE 4

2-(6-Nitro-2-quinolinyl)-6-acetyldecahydropyrrolo [3,4-d]-azepine

To a methanol (15 ml) solution of 2-(t-butoxycarbonyl)-6-benzyldecahydropyrrolo[3,4-d]azepine (this compound had been prepared by the method as described in WO 99/40070) (680 mg), palladium-on-carbon (500 mg) was added and stirred under gaseous hydrogen stream (50 psi) an overnight at room temperature. The palladium-on-carbon was removed by filtration through Celite®, and the filtrate was concentrated under reduced pressure. The resulting residue was dissolved in chloroform (10 ml), to which triethylamine (516 mg) and acetyl chloride (200 mg) were added, followed by an hour's stirring at room temperature. The reaction liquid was washed with saturated aqueous sodium carbonate solution, and the organic layer was dried over anhydrous magnesium sulfate. Distilling the solvent off under reduced pressure, the resulting residue was dissolved in trifluoroacetic acid (5 ml) and stirred for 2 hours at room temperature. Distilling the solvent off under reduced pressure, the residue was dissolved in DMF (10 ml). To the solution 2-chloro-6-nitroquinoline (283 mg) and potassium carbonate (1.17 g) were added and stirred an overnight at 90° C. Distilling the solvent off under reduced pressure and subjecting the resulting residue to silica gel column chromatography (chloroform:methanol=10:1), the title compound (424 mg) was obtained. ESI-MS Found: m/z 355[M+H]+

REFERENTIAL EXAMPLE 5

(3R)-N-methyl-N-[1-(6-nitro-2-quinolinyl)-3-pyrrolidinyl]-acetamide

Referential Example 3 was repeated except that the isobutyryl chloride which was used in Referential example 3-(4) was replaced with acetyl chloride, to provide the title compound.
1H-NMR(300 MHz,CDCl$_3$,δppm):2.05-2.40(5H,m), 2.85-3.05(3H,m), 3.40-4.10(4H,m), 4.50-5.55(1H,m), 6.75-6.90(1H,m), 7.60-7.75(1H,m), 7.90-8.05(1H,m), 8.20-8.40 (1H,m),8.50-8.65(1H,m).

REFERENTIAL EXAMPLE 6

(3R)-N-methyl-N-[1-(6-nitro-2-quinolinyl)-3-pyrrolidinyl]-propanamide

Referential Example 3 was repeated except that the isobutyryl chloride which was used in Referential example 3-(4) was replaced with propionyl chloride, to provide the title compound.
1H-NMR(300 MHz,CDCl$_3$,δppm):1.10-1.30(3H,m), 2.10-2.60(4H,m), 2.85-3.05 (3H,m), 3.40-4.10(4H,m), 4.50-5.55(1H,m), 6.75-6.90(1H,m), 7.60-7.75(1H,m), 7.90-8.05 (1H,m), 8.20-8.40(1H,m), 8.50-8.65(1H,m).

REFERENTIAL EXAMPLE 7

(3R)-N-methyl-N-[1-(6-nitro-2-quinolinyl)-3-pyrrolidinyl]-methanesulfonamide

Referential Example 3 was repeated except that the isobutyryl chloride which was used in Referential example 3-(4) was replaced with methanesulfonyl chloride, to provide the title compound.
1H-NMR(300 MHz,CDCl$_3$,δppm):2.15-2.45(2H,m), 2.85-3.00(3H,m), 3.55-3.75(4H,m), 3.80-4.10(2H,m), 4.65-4.80(1H,m), 6.75-6.90(1H,m), 7.60-7.75(1H,m), 7.90-8.05 (1H,m), 8.20-8.35(1H,m), 8.50-8.60(1H,m).

REFERENTIAL EXAMPLE 8

2-[Isopropyl(methyl)amino]-6-nitroquinoline

Referential Example 2-(6) was repeated except that 3-oxo-2,7-diazaspiro[4,4]nonane was replaced with N-isopropyl(methyl)amine, to provide the title compound. ESI-MS Found:m/z 246[M+H]+

REFERENTIAL EXAMPLE 9

N-2-[methyl(tetrahydro-3-furanyl)amino]-6-nitroquinoline

Referential Example 2-(6) was repeated except that 3-oxo-2,7-diazaspiro[4,4]nonane was replaced with N-methyl(tetrahydro-3-furanyl)amine, to provide the title compound. ESI-MS Found:m/z 274[M+H]+

REFERENTIAL EXAMPLE 10

5-Phenylpyrimidine-2-carboxylic acid

To a solution of 5-bromopyrimidine-2-carboxylic acid (5.01 g) and phenylboronic acid (3.61 g) in ethylene glycol dimethyl ether (150 ml), 2M aqueous sodium carbonate solution (100 ml) and tetralcistriphenylphosphine palladium (1.42 g) were added and stirred for 5 hours at 80° C. To the reaction liquid aqueous sodium hydrogencarbonate solution was added, diluted with water and washed with diethyl ether. To the aqueous layer 10% aqueous phosphoric acid was added to drop pH of the system to 4, followed by extraction with ethyl acetate, washing with saturated saline, drying over anhydrous sodium sulfate and concentration under reduced pressure. Thus the title compound (3.66 g) was obtained as white crystals. ESI-MS Found:m/z 201[M+H]+ ESI-MS Found:m/z 199[M−H]−

REFERENTIAL EXAMPLE 11

5-(4-Fluorophenyl)pyrimidine-2-carboxylic acid

Referential Example 10 was repeated except that phenylboronic acid was replaced with 4-fluorophenylboronic acid, to provide the title compound. ESI-MS Found:m/z 219[M+H]+ ESI-MS Found:m/z 217[M−H]−

REFERENTIAL EXAMPLE 12

5-(3-Fluorophenyl)pyrimidine-2-carboxylic acid

Referential Example 10 was repeated except that phenylboronic acid was replaced with 3-fluorophenylboronic acid, to provide the title compound. ESI-MS Found: m/z 219[M+H]+ ESI-MS Found:m/z 217[M−H]−

EXAMPLE 1

5-(4-Fluorophenyl)-N-[2-(1-methyl-2-oxo-1,7-diazaspiro[4,4]-nonan-7-yl)-6-quinolinyl]-2-pyrimidinecarboxamide To a methanol (5 ml) solution of the compound as obtained in Referential Example 1 (80 mg), palladium-on-carbon (10 mg) was added, and stirred for an hour at room temperature in hydrogen atmosphere. The reaction liquid was filtered and the solvent was distilled off under reduced pressure. The residue was dissolved in chloroform (10 ml), to which the compound as obtained in Referential Example 11 (53 mg), triethylamine (70 μl) and 2-chloro-1,3-dimethylimidazolium chloride (41 mg) were added. The resulting mixture was stirred an overnight at room temperature. Water was added to the reaction liquid which then was extracted with ethyl acetate. The ethyl acetate layer was dried over anhydrous sodium sulfate and concentrated under reduced pressure. The residue was subjected to column chromatography (chloroform:methanol=100:1) to provide the title compound (64 mg) as a yellow solid. 1H-NMR(400 MHz,CDCl$_3$,δppm):1.95-2.10(2H,m), 2.13-2.24(1H,m), 2.36-2.55(3H,m), 2.87(3H,s), 3.60-3.78 (3H,m), 3.85-3.94(1H,m), 6.74(1H,d,J=9.2 Hz), 7.22-7.30 (2H,m), 7.60-7.75(4H,m), 7.96(1H,d,J=9.2 Hz), 9.07(2H,s), 10.01(1H,s).

EXAMPLE 2

5-(4-Fluorophenyl)-N-[2-(7-methyl-8-oxo-2,7-diazaspiro[4,4]-nonan-2-yl)-6-quinolinyl]-2-pyrimidinecarboxamide hydrochloride Example 1 was repeated except that the compound as obtained in Referential Example 1 was replaced with that as obtained in Referential Example 2, and the resulting compound was treated with 4N-hydrochloric acid-ethyl acetate to provide the title compound. 1H-NMR(300 MHz,d6-DMSO, δppm):2.15(2H,m), 2.44(2H,brs), 2.75(3H,s), 3.56(2H,m), 3.85(4H,m), 7.27(1H,m), 7.45(2H,m), 8.01(2H,m),8.17(2H, m), 8.46(1H,m), 8.62 (1H,brs), 9.36(2H, s), 11.18(1H, s). ESI-MS Found:m/z 497[M+H]+

EXAMPLE 3

N-(2-[(3R)-3-[isobutyryl(methyl)amino]-1-pyrrolidinyl]-6-quinolinyl)-5-phenyl-2-pyrimidinecarboxamide To a solution of the compound as obtained in Referential Example 3 (10.2 g) in tetrahydrofuran (150 ml), 20% palladium hydroxide-on-carbon (4.19 g) was added in nitrogen atmosphere, followed by an overnight's stirring in hydrogen atmosphere of one atmospheric pressure. The reaction system was nitrogen-exchanged to suspend the reaction, and the reaction liquid was filtered with Celite®. The filtrate was concentrated under reduced pressure. To a solution of the residue in dimethylformamide (70 ml), phenylpyrimidinecarboxylic acid (5.97 g) as obtained in Referential Example 10 and triethylamine (8.3 ml) were added at 0° C., followed by further dropwise addition of a solution of 2-chloro-1,3-dimethylimidazolium chloride (6.55 g) in dimethylformamide (30 ml) and subsequent an hour's stirring. After addition of aqueous sodium hydrogencarbonate solution to the reaction liquid and dilution with water, the formed solid was recovered by filtration. The solid was subjected to silica gel column chromatography (chloroform:methanol=95:5) and recrystallized from ethyl acetate, to provide the title compound (7.65 g) as yellow crystals. 1H-NMR(400 MHz,d6-DMSO,δppm): 1.05-1.08(6H,m), 2.05-2.25(2H,m), 2.78(3/2H,s), 2.96(3/2H,s), 2.82-3.10(1H,m), 3.35-3.55(2H,m), 3.65-3.87(2H,m), 4.784.89(1/2H,m), 5.13-5.25(1/2H,m), 6.88-6.93(1H,m), 7.51-7.60(4H,m), 7.90-7.92(3H,m), 8.01(1H,d,J=8.8 Hz), 8.36(1H,d,J=2.4 Hz), 9.34(2H,s), 10.85(1H,s). ESI-MS Found:m/z 496[M+H]+

EXAMPLE 4

N-[2-(6-acetyldecahydropyrrolo[3,4-d]azepin-2-yl)-6-quinolinyl]-5-phenyl-2-pyrimidinecarboxamide Example 3 was repeated except that the compound as obtained in Referential Example 4 was used in place of that as obtained in Referential Example 3, to provide the title compound. 1H-NMR(300 MHz,d6-DMSO,δppm):1.70-1.82 (5H,m), 2.01(3H,s), 2.48 and 3.18(4H,m), 3.32-3.67(5H,m), 6.84(1H,d,J=8.7 Hz), 7.54(4H,m), 7.91(3H,m), 8.30(2H,m), 9.34(2H,s), 10.83(1H,s). ESI-MS Found:m/z 507[M+H]+

EXAMPLE 5

N-(2-[(3R)-3-[acetyl(methyl)amino]-1-pyrrolidinyl]-6-quinolinyl)-5-phenyl-2-pyrimidinecarboxamide Example 3 was repeated except that the compound as obtained in Referential Example 5 was used in place of that as obtained in Referential Example 3, to provide the title compound. 1H-NMR(300 MHz,d6-DMSO,δppm):1.95-2.30 (5H,m), 2.70-2.95(3H,m), 3.25-3.35(3H,m), 3.35-3.60(2H, m), 3.60-3.90(2H,m), 4.60-5.25(1H,m), 6.85-6.95(1H,m), 7.45-7.65(4H,m), 7.85-8.10(4H,m), 8.36(1H,s), 9.36(2H,s), 10.85(1H,s). ESI-MS Found:m/z 467[M+H]+

EXAMPLE 6

5-Phenyl-N-(2-[(3R)-3-[propionyl(methyl)amino]-1-pyrrolidnyl]-6-quinolinyl)-2-pyrimidinecarboxamide Example 3 was repeated except that the compound as obtained in Referential Example 6 was used in place of that as obtained in Referential Example 3, to provide the title compound. 1H-NMR(300 MHz,d6-DMSO,δppm):0.95-1.10 (3H,m), 2.00-2.25(2H,m), 2.25-2.50(2H,m), 2.70-2.95(3H, m), 3.35-3.60(2H,m), 3.60-3.85(2H,m), 4.65-5.30(1H,m), 6.85-6.95(1H,m), 7.45-7.65(4H,m), 7.85-8.10(4H,m), 8.36 (1H,s), 9.36(2H,s), 10.84(1H,s). ESI-MS Found:m/z 481 [M+H]+

EXAMPLE 7

N-(2-[(3R)-3-[methanesulfonyl(methyl)amino]-1-pyrroldinyl]-6-quinolinyl)-5-phenyl-2-pyrimidinecarboxamide Example 3 was repeated except that the compound as obtained in Referential Example 7 was used in place of that as obtained in Referential Example 3, to provide the title compound. 1H-NMR(300 MHz,d6-DMSO,δppm):2.10-2.30 (2H,m), 2.79(3H,s), 2.99(3H,s), 3.40-3.60(2H,m), 3.70-3.90 (2H,m), 4.454.60(1H,m), 6.85-6.95(1H,m), 7.45-7.65(4H, m), 7.85-8.10(4H,m), 8.36(1H,s), 9.36(2H,s), 10.85(1H,s). ESI-MS Found:m/z 503[M+H]+

EXAMPLE 8

N-(2-[(3R)-3-[methoxycarbonyl(methyl)amino]-1-pyrrolidinyl]-6-quinolinyl)-5-phenyl-2-pyrimidinecarboxamide (1) N-(2-[(3R)-3-[tert-butoxycarbonyl(methyl)amino]-1-pyrrolidinyl]-6-quinolinyl)-5-phenyl-2-pyrimidinecarboxamide Example 3 was repeated except that tert-butyl (3R)-N-methyl-N-[1-(6-nitro-2-quinolinyl)-3-pyrrolidinyl]carbamate as obtained in Referential Example 3-(3) was used in place of the compound as obtained in Referential Example 3, to provide the title compound.

(2) N-(2-[(3R)-3-[methoxycarbonyl(methyl)amino]-1-pyrrolidinyl]-6-quinolinyl)-5-phenyl-2-pyrimidinecarboxamide The title compound was obtained by repeating Referential Example 3-(4) except that the compound as obtained in Referential Example 3-(3) was replaced with the compound as obtained in above (1) and isobutyryl chloride was replaced with methyl chlorocarbonate. 1H-NMR(400 MHz,CDCl$_3$, δppm):2.18-2.27(2H,m), 2.90(3H,s), 3.53-3.61 (2H,m), 3.75 (3H,s),3.82-3.90(2H,m), 5.00(1H,br,s), 6.75(1H,d,J=9.2

Hz), 7.52-7.59(3H,m), 7.65-7.74(4H,m), 7.94(1H,d,J=9.2 Hz), 8.43(1H,'s), 9.12(2H,s), 10.04(1H,s). ESI-MS Found: m/z 483[M+H]+

EXAMPLE 9

N-(2-[(3R)-3-[[(dimethylamino)carbonyl](methyl) amino]-1-pyrrolidinyl]-6-quinolinyl)-5-phenyl-2-pyrimidinecarboxamide The title compound was obtained by repeating Referential Example 3-(4) except that the compound as obtained in Referential Example 3-(3) was replaced with the compound as obtained in Example 8-(1) and isobutyryl chloride was replaced with dimethyl-carbamoyl chloride. 1H-NMR(400 MHz,CDCl$_3$,δppm):1.59(6H,s), 2.12-2.21 (1H,m), 2.24-2.35 (1H,m), 2.82(3H,s), 3.49-3.62(2H,m), 3.82-3.90(1H,m), 3.92-4.00(1H,m), 4.464.54(1H,m), 6.75(1H,d,J=9.2 Hz), 7.50-7.57(3H,m), 7.64-7.72(4H,m), 7.92(1H,d,J=8.8 Hz), 8.40(1H,brs), 9.11(2H,s), 10.02(1H,s). ESI-MS Found:m/z 496[M+H]+

EXAMPLE 10

N-(2-[isoropyl(methyl)amino]-6-quinolinyl)-5-phenyl-2-pyrimidinecarboxamide

The title compound was obtained by repeating Example 3, except that the compound as obtained in Referential Example 3 was replaced with that as obtained in Referential Example 8. 1H-NMR(400 MHz,CDCl$_3$,δppm):1.24(6H,d,J=6.8 Hz), 3.01 (3H,s), 4.98(1H,septet,J=6.8Hz), 6.91(1H,d,J=9.2 Hz), 7.49-7.57(3H,m), 7.62-7.69(4H,m), 7.89(1H,d,J=9.2 Hz), 8.38(1H,s), 9.10(2H,s), 10.00(1H,s). ESI-MS Found:m/z 398 [M+H]+

EXAMPLE 11

5-(4-Fluorophenyl)-N-(2-[(3R)-3-[isobutyryl(methyl)amino]-1-pyrrolidinyl]-6-quinolinyl)-2-pyrimidinecarboxamide Example 1 was repeated except that the compound as obtained in Referential Example 1 was replaced with the one as obtained in Referential Example 3. 1H-NMR(400 MHz, d6-DMSO,δppm):1.00-1.07(6H,m), 2.06-2.25(2H,m), 2.77 (3/2H,s), 2.82-2.91(1/2H,m), 2.96(3/2H,s), 3.00-3.11(1/2H, m), 3.37-3.57(2H,m), 3.66-3.84(2H,m), 4.78-4.88(1/2H,m), 5.12-5.23(1/2H,m), 6.88-6.94(1H,m), 7.40-7.44(2H,m), 7.54 (1H,d,J=9.2 Hz), 7.90(1H,dd,J=9.2,2.0 Hz), 7.96-8.02(3H, m), 8.34(1H,d,J=2.0 Hz), 9.33(2H,s), 10.83(1H,s). ESI-MS Found:m/z 513[M+H]+

EXAMPLE 12

N-(2-[(3R)-3-[acetyl(methyl)amino]-1-pyrrolidinyl]-6-quinolinyl)-5-(4-fluorophenyl)-2-pyrimidinecarboxamide Example 1 was repeated except that the compound as obtained in Referential Example 1 was replaced with the one as obtained in Referential Example 5. 1H-NMR(300 MHz, d6-DMSO,δppm): 1.95-2.25(5H,m), 2.70-2.95(3H,m), 3.25-3.35(3H,m), 3.35-3.60(2H,m), 3.60-3.90(2H,m), 4.60-5.30 (1H,m), 6.85-6.95(1H,m), 7.35-7.60(3H,m), 7.85-8.10(4H, m), 8.36(1H,s), 9.35(2H,s), 10.85(1H,s). ESI-MS Found: m/z 485[M+H]+

EXAMPLE 13

5-(4-Fluorophenyl)-N-(2-[methyl(tetrahydro-3-furanyl)amino]-6-quinolinyl)-2-pyrimidinecarboxamide Example 1 was repeated except that the compound as obtained in Referential Example 1 was replaced with the one as obtained in Referential Example 9. 1H-NMR(400 MHz, CDCl$_3$,δppm):1.94-2.04(1H,m), 2.32-2.42(1H,m), 3.10(3H, s), 3.75-3.96(3H,m), 4.08-4.15(1H,m), 5.64-5.74(1H,m), 6.94(1H,d,J=9.2 Hz), 7.22-7.30(2H,m), 7.60-7.74(4H,m), 7.94(1H,d,J=9.2 Hz), 8.41(1H,s), 9.06(2H,s), 10.00(1H,s). ESI-MS Found:m/z 444[M+H]+

EXAMPLE 14

5-(3-Fluorophenyl)-N-(2-[(3R)-3-[isobutyryl(methyl)amino]-1-pyrrolidinyl]-6-quinolinyl)-2-pyrimidinecarboxamide Example 3 was repeated except that 5-phenylpyrimidine-2-carboxylic acid was replaced with the compound as obtained in Referential Example 12, to provide the title compound. 1H-NMR(400 MHz,d6-DMSO,δppm):1.01-1.07 (6H,m), 2.07-2.25(2H,m), 2.77(3/2H,s), 2.83-2.91(1/2H,m), 2.95(3/2H,s), 3.00-3.08(1/2H,m), 3.38-3.56(2H,m), 3.66-3.85(2H,m), 4.78-4.88(1/2H,m), 5.12-5.23(1/2H,m), 6.89-6.94(1H,m), 7.34-7.39(1H,m), 7.54(1H,d,J=8.8 Hz), 7.62 (1H,dd,J=8.0,6.0 Hz), 7.78(1H,d,J=8.0 Hz), 7.85(1H,dt, J=10.4,2.0 Hz), 7.90(1H,dd,J=9.2,2.0 Hz), 8.01 (1H,d,J=8.8 Hz), 8.34(1H,d,J=2.0 Hz), 9.38(2H,s), 10.84(1H,s). ESI-MS Found:m/z 513[M+H]+

PHARMACOLOGICAL TEST EXAMPLES

Medical utility of compounds of the present invention is verified, for example, by the following pharmacological test examples.

Pharmacological Test Example 1

MCH Binding Inhibition Test

A human MCH-1R encoding cDNA sequence [FEBS Letters, Vol. 398, p. 253 (1996); Biochimica et Biophisica Acta, Vol. 1401, p. 216 (1998)] was cloned to plasmid vector pEF/mic/cyto (Invitrogen Corporation). The obtained expression vector was transfected to a host cell CHO-K1 (American Type Culture Collection) using lipofectamine plus reagent (Life Technology Inc.) to provide MCH-1R expression cells.

Membrane samples prepared from the MCH-1R expression cells were incubated with each test compound and 50 pM of [$^{125}$I]MCH (NEN Co.), in an assay buffer (50 mM Tris buffer comprising 10 mM magnesium chloride, 2 mM ethylenediamine tetraacetate, 0.01% bacitracin and 0.2% bovine serum albumin; pH 7.4) at 25° C. for an hour, followed by filtration through Glass Filter GF/C (Wattman Co.). After washing the glass filter with 50 mM Tris buffer (pH7.4) comprising 10 mM magnesium chloride, 2 mM ethylenediamine tetraacetate and 0.04% Tween-20, radio activity on the glass filter was measured. Non-specific binding was measured in the presence of 1 μM human MCH and 50% inhibition concentration (IC$_{50}$ value) of each test compound to specific [$^{125}$I] MCH binding was determined. The results were as shown in Table 2.

TABLE 2

| Test Compound | IC$_{50}$ (nM) |
|---|---|
| Example 1 | 8.0 |
| Example 3 | 4.1 |
| Example 9 | 3.7 |

Test Example 2

Antagonism Test to MCH-Induced Feeding Behavior

Ketamine-xylazine anesthetized (74 and 11 mg/kg single intraperitoneal administration) male SD rats (9-12 weeks old) were inserted with chronic guide cannule (26 gauge) into their third ventricle as fixed at a set cerebral location with dental resin. The position of the front end of the guide cannula was set to be 2.2 mm behind the bregma on median line and at a depth of 8 mm from the cranial surface. After two weeks' recovery term, the rats were fed with high fat diet for about 4 hours to satiation. Thereafter a needle (33 gauge) which was connected to a microsyringe was inserted into the guide cannula and through which melanin concentrating hormone (MCH, 5 μg/1 μL/head, as dissolved in artificial liquor cerebrospinalis) was administered into each rat's third ventricle. The compound of Example 3 (10 or 30 mg/kg) as suspended in 0.5% aqueous methylcellulose solution was orally administered to the rats an hour before the MCH administration. The rats were successively fed with high fat diet, and their feed intake during the two hours following the MCH administration was measured.

FIG. 1 shows the feed intake by the high fat diet satiated rats, to which the compound of the present invention had been orally administered and an hour thereafter MCH had been administered intraventricularly, during the two hours following said MCH administration, i.e., shows the rats' feed intake (g) per the two hours, where 1) said Example 3 compound was not administered, 2) Example 3 compound was administered at a rate of 10 mg/kg, and 3) Example 3 compound was administered at a rate of 30 mg/kg.

As demonstrated on FIG. 1, the compound of the present invention dose-dependently inhibited increase in the amount of feed intake induced by the MCH which was administered to the rats' third ventricle. In this test, the feed intake in the case where MCH and artificial liquor cerebrospinalis (aCSF) alone was administered in place of the compound of the present invention was used as the reference.

INDUSTRIAL UTILIZABLITY

The compounds of the present invention exhibit MCH-1R antagonistic action and are useful as preventing or treating agents of metabolic disorders represented by obesity, diabetes, hormone disorder, hyperlipidemia, gout, fatty liver, hepatitis and cirrhosis; cardiovascular disorders, represented by stenocardia, acute or congestive heart failure, myocardial infarction, coronary atherosclerosis, hypertension, renal diseases and electrolyte abnormality; central nervous system or peripheral nervous system disorders represented by bulimia, emotional disturbance, depression, anxiety, epilepsy, delirium, dementia, schizophrenia, attention-deficit hyperactivity disorder, memory impairment, sleep disorders, cognitive failure, dyskinesia, paresthesias, smell disorders, morphine tolerance, drug dependence and alcoholism; reproductive disorders represented by infertility, preterm labor and sexual dysfunction; digestive disorders; respiratory disorders; cancer or pigmentation.

The invention claimed is:

1. A compound of general formula [I]:

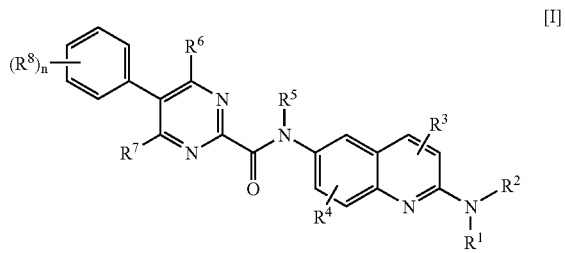

wherein:

$R^1$ and $R^2$ are each independently selected from the group consisting of:
(1) optionally hydroxyl- or halogen-substituted lower alkyl,
(2) optionally $R^9$-substituted 3 to 6-membered cycloalkyl, and
(3) optionally $R^9$-substituted 4 to 6-membered heterocycloalkyl, or
(4) $R^1$ and $R^2$ together form a 4 to 11-membered crosslinking, non-crosslinking or spiro ring aliphatic nitrogen-containing heterocycle, with the nitrogen atom to which they bind, one or two optional hydrogen atoms in the aliphatic nitrogen-containing heterocycle being optionally substituted with $R^9$;

$R^3$, $R^4$, $R^6$ and $R^7$ are each independently selected from the group consisting of:
(1) hydrogen,
(2) hydroxyl,
(3) halogen, and
(4) optionally halogen-substituted lower alkyl;

$R^5$ stands for:
(1) hydrogen, or
(2) optionally halogen-substituted lower alkyl;

each $R^8$ is independently selected from the group consisting of:
(1) halogen,
(2) lower alkyl, and
(3) lower alkyloxy;

$R^9$ is selected from the group consisting of hydroxyl, amino, mono-lower alkylamino, di-lower alkylamino, optionally hydroxyl- or halogen-substituted lower alkyl, (lower alkyloxycarbonyl)amino, lower alkyloxycarbonyl-(lower alkyl)amino, lower alkylcarbonylamino, lower alkylcarbonyl(lower alkyl)amino, mono-lower alkylcarbamoyl-(lower alkyl)amino, di-lower alkylcarbamoyl(lower alkyl)amino, lower alkylsulfonylamino, lower alkylsulfonyl(lower alkyl)amino, oxo and 2-oxopyrrolidinyl; and n is 0, 1, 2, 3 or 4;

or a pharmaceutically acceptable salt thereof.

2. The compound according to claim 1, wherein: $R^1$ is lower alkyl, and $R^2$ is selected from the group consisting of optionally hydroxyl-substituted lower alkyl, tetrahydrofuranyl and optionally $R^9$-substituted pyrrolidinyl, or a pharmaceutically acceptable salt thereof.

3. The compound according to claim 1, wherein: the 4 to 11-membered crosslinking, non-crosslinking or spiro ring aliphatic nitrogen-containing heterocycle formed by $R^1$ and $R^2$ together with the nitrogen atom to which they bind is represented by a formula (A):

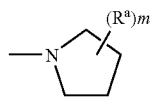

wherein $R^a$ is $R^9$ or two $R^a$s together form —(CH$_2$)x-(NH)—(CH$_2$)y-, hydrogen in the substituent group may optionally be substituted with lower alkyl, lower alkylcarbonyl or oxo, x and y are each independently selected from 0, 1, 2, 3 or 4, provided that $3 \leq x+y \leq 4$, and m is selected from 0, 1 or 2; or a pharmaceutically acceptable salt thereof.

4. The compound according to claim 3, wherein:
$R^a$ is selected from the group consisting of lower alkylcarbonyl(lower alkyl)amino, lower alkylsulfonyl(lower alkyl)amino, lower alkyloxycarbonyl(lower alkyl)amino, and di-lower alkylcarbamoyl(lower alkyl)amino, and
m=1;
or a pharmaceutically acceptable salt thereof.

5. The compound according to claim 3, wherein: m=2, and the two $R^a$s together form a group selected from the group consisting of:

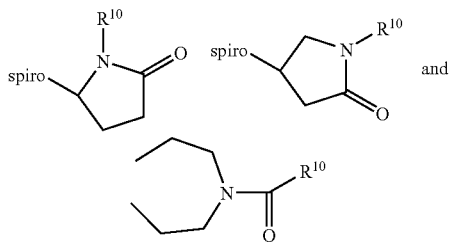

wherein: $R^{10}$ is selected from lower alkyl and lower alkylcarbonyl;
or a pharmaceutically acceptable salt thereof.

6. The compound according to claim 3, wherein: the aliphatic nitrogen-containing heterocycle represented by the formula (A) is selected from the group consisting of:
1-methyl-2-oxo-1,7-diazaspiro[4.4]nonan-7-yl, 7-methyl-8-oxo-2,7-diazaspiro[4.4]nonan-2-yl, 3-[acetyl(methyl)amino]pyrrolidin-1-yl, 3-[propionyl(methyl)amino]pyrrolidin-1-yl, 3-[isobutyryl(methyl)-amino]pyrrolidin-1-yl, 3-[methanesulfonyl(methyl)amino]pyrrolidin-1-yl, 3-[methoxycarbonyl(methyl) amino]pyrrolidin-1-yl, 3-{[(dimethylamino)carbonyl](methyl)amino}pyrrolidin-1-yl, 6-acetyldecahydro-pyrrolo[3,4-d[azepin-2-yl, and 2-oxo]1.3']bipyrrolidinyl-1'-yl;
or a pharmaceutically acceptable salt thereof.

7. The compound according to claim 1, wherein: $R^8$ is a fluorine atom or a methoxy group, or a pharmaceutically acceptable salt thereof.

8. The compound according to claim 1, wherein: selected from the group consisting of:
(1) 5-(4-fluorophenyl)-N-[2-(1-methyl-2-oxo-1,7-diazaspiro[4,4]nonan-7-yl)-6-quinolinyl]-2-pyrimidinecarboxamide,
(2) 5-(4-fluorophenyl)-N-[2-(7-methyl-8-oxo-2,7-diazaspiro[4,4]-nonan-2-yl)-6-quinolinyl]-2-pyrimidinecarboxamide,
(3) N-(2-[(3R)-3-[isobutyryl(methyl)amino]-1-pyrrolidinyl]-6-quinolinyl)-5-phenyl-2-pyrimidine carboxamide,
(4) N-[2-(6-acetyldecahydropyrrolo[3,4-d]azepin-2-yl)-6-quinolinyl]-5-phenyl-2-pyrimidine carboxamide,
(5) N-[2-[(3R)-3-[acetyl(methyl)amino]-1-pyrrolidinyl]-6-quinolinyl)-5-phenyl-2-pyrimidine carboxamide,
(6) 5-phenyl-N-(2-[(3R)-3-[propionyl(methyl)amino]-1-pyrrolidinyl]-6-quinolinyl)-2-pyrimidine carboxamide,
(7) N-(2-[(3R)-3-[methanesulfonyl(methyl)amino]-1-pyrrolidinyl]-6-quinolinyl)-5-phenyl-2-pyrimidine carboxamide,
(8) N-(2-[(3R)-3-[methoxycarbonyl(methyl)amino-1-pyrrolidinyl]-6-quinolinyl)-5-phenyl-2-pyrimidine carboxamide,
(9) N-(2-[(3R)-3-[[(dimethylamino)carbonyl)](methyl)amino]-1-pyrrolidinyl]-6-quinolinyl)-5-phenyl-2-pyrimidinecarboxamide,
(10) N-(2-[isopropyl(methyl)amino]-6-quinolinyl)-5-phenyl-2-pyrimidinecarboxamide,
(11) 5-(4-fluorophenyl)-N-(2-[(3R)-3-[isobutyryl(methyl)amino]-1-pyrrolidinyl]-6-quinolinyl)-2-pyrimidinecarboxamide,
(12) N-(2-[(3R)-3-[acetyl(methyl)amino]-1-pyrrolidinyl]-6-quinolinyl)-5-(4-fluorophenyl)-2-pyrimidine carboxamide,
(13) 5-(4-fluorophenyl)-N-(2-[methyl(tetrahydro-3-furanyl)amino]-6-quinolinyl)-2-pyrimidine carboxamide and
(14) 5-(3-fluorophenyl)-N-(2-[(3R)-3-[isobutyryl(methyl)amino]-1-pyrrolidinyl]-6-quinolinyl)-2-pyrimidine carboxamide, or a pharmaceutically acceptable salt thereof.

9. A method for treating obesity in a human subject in need of such treatment comprising administering to the human subject of a therapeutically effective amount of a compound according to claim 1, or a pharmaceutically acceptable salt thereof.

10. A pharmaceutical composition comprising a compound according to claim 1, or a pharmaceutically acceptable salt thereof, and a pharmaceutically acceptable carrier.

11. A process for preparing the compound of general formula [I] of claim 1, wherein: $R^1$, $R^2$, $R^3$, $R^4$, $R^5$, $R^6$, $R^7$, $R^8$ and n have the same significations as given in claim 1,
which comprises the step of subjecting a compound of a general formula [II]:

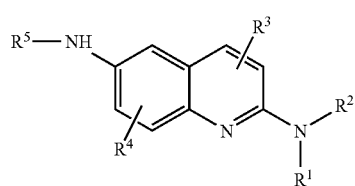

wherein $R^1$, $R^2$, $R^3$, $R^4$ and $R^5$ are as defined in claim 1; and a compound of a general formula [III]

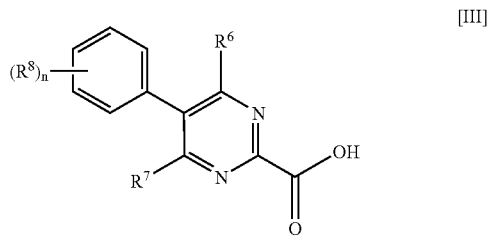

wherein $R^6$, $R^7$, $R^8$ and n are as defined in claim 1; to an amidation reaction.

* * * * *